(12) United States Patent
Katsuragi et al.

(10) Patent No.: US 12,220,160 B2
(45) Date of Patent: Feb. 11, 2025

(54) CONTROL DEVICE, TREATMENT SYSTEM, RESIDUAL-HEAT DETERMINING METHOD, AND COMPUTER READABLE RECORDING MEDIUM

(71) Applicant: OLYMPUS CORPORATION, Hachioji (JP)

(72) Inventors: Toshifumi Katsuragi, Tokyo (JP); Danilo Legaspi, Tokyo (JP); Tsuyoshi Hayashida, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1088 days.

(21) Appl. No.: 17/083,822

(22) Filed: Oct. 29, 2020

(65) Prior Publication Data
US 2021/0038295 A1  Feb. 11, 2021

Related U.S. Application Data

(63) Continuation of application No. PCT/JP2018/041364, filed on Nov. 7, 2018.

(51) Int. Cl.
*A61B 18/12* (2006.01)
*A61B 18/14* (2006.01)
(Continued)

(52) U.S. Cl.
CPC ..... *A61B 18/1445* (2013.01); *A61B 2017/00017* (2013.01); *A61B 2017/00119* (2013.01);
(Continued)

(58) Field of Classification Search
CPC ............ A61B 18/1445; A61B 18/1206; A61B 18/1482; A61B 18/085; A61B 18/1233;
(Continued)

(56) References Cited

U.S. PATENT DOCUMENTS 5,558,671 A * 9/1996 Yates ................. A61B 18/1206
606/50
6,306,131 B1 10/2001 Hareyama et al.
(Continued)

FOREIGN PATENT DOCUMENTS

| JP | 2000-107197 A | 4/2000 |
| WO | 2013/088891 A1 | 6/2013 |
| WO | 2016/021579 A1 | 2/2016 |

OTHER PUBLICATIONS

Feb. 5, 2019 Search Report issued in International Patent Application No. PCT/JP2018/041364.

*Primary Examiner* — Thomas A Giuliani
(74) *Attorney, Agent, or Firm* — Oliff PLC

(57) ABSTRACT

A control device includes a processor configured to: execute a sealing control mode in which electrical power to seal a living tissue by heating the living tissue at a first temperature is supplied, and an incision control mode in which electrical power to incise the living tissue by heating the living tissue at a second temperature higher than the first temperature is supplied; calculate elapsed time, as an index value, since it has reached the second temperature by executing the incision control mode; compare the index value and a threshold; determine a residual heat level of an end effector based on a result of comparison between the index value and the threshold; and perform, based on a determination result of the residual heat level, at least one of: notification of information indicating a warning from a notifying unit; and adjustment of electrical power supplied to the end effector.

19 Claims, 14 Drawing Sheets

(51) Int. Cl.
*A61B 17/00* (2006.01)
*A61B 18/00* (2006.01)

(52) U.S. Cl.
CPC ............... *A61B 2018/00601* (2013.01); *A61B 2018/0063* (2013.01); *A61B 2018/00666* (2013.01); *A61B 2018/00827* (2013.01); *A61B 2018/00892* (2013.01); *A61B 2018/1467* (2013.01)

(58) Field of Classification Search
CPC ...... A61B 18/1442; A61B 2017/00017; A61B 2017/00119; A61B 2018/00791; A61B 2018/00886; A61B 2018/1452; A61B 2018/00636; A61B 2018/00702; A61B 2018/00708; A61B 2018/00601; A61B 2018/0063; A61B 2018/00666; A61B 2018/00404; A61B 2018/00607; A61B 2018/00648; A61B 2018/00684; A61B 2018/00714; A61B 2018/00898; A61B 2018/00958; A61B 2018/00994; A61B 2018/00642
USPC ........ 606/34, 37, 38, 41, 42, 50–52; 607/98, 607/99, 115, 116
See application file for complete search history.

(56) References Cited

U.S. PATENT DOCUMENTS

| | | | |
|---|---|---|---|
| 2008/0255642 A1* | 10/2008 | Zarins | A61N 5/0601 607/99 |
| 2012/0136347 A1* | 5/2012 | Brustad | A61B 18/1206 606/46 |
| 2013/0338656 A1 | 12/2013 | Irisawa et al. | |
| 2016/0310207 A1* | 10/2016 | Honda | A61B 18/1445 |
| 2018/0116709 A1 | 5/2018 | Honda et al. | |

* cited by examiner

CONTROL DEVICE, TREATMENT SYSTEM, RESIDUAL-HEAT DETERMINING METHOD, AND COMPUTER READABLE RECORDING MEDIUM

This application is a continuation of International Application No. PCT/JP2018/041364, filed on Nov. 7, 2018, the entire contents of which are incorporated herein by reference.

BACKGROUND

The present disclosure relates to a control device, a treatment system, a residual-heat determining method, and a computer-readable recording medium.

Medical devices that applies a treatment energy from an end effector to a portion to be treated (hereinafter, denoted as target portion) in a living tissue to thereby treat the target portion have been known (for example, International Publication Pamphlet No. WO2013/088891).

In a medical device described in WO2013/088891, an end effector includes a heater that generates heat according to a supply of electric power, and a pair of high frequency electrodes. In the medical device, by supplying an electric power to the heater, a heat energy, which is a treatment energy, is applied to a target portion from the end effector. Moreover, in the medical device, by supplying an electric power to a portion between the pair of high frequency electrodes, a high frequency energy, which is a treatment energy, is applied to a target portion from the end effector.

SUMMARY

According to one aspect of the present disclosure, there is provided a control device for being used with a treatment tool including an end effector configured to apply a treatment energy to a living tissue for treatment of the living tissue, the control device comprising a processor configured to: execute a sealing control mode in which electrical power to seal the living tissue by heating the living tissue at a first temperature is supplied to the end effector, and an incision control mode in which electrical power to incise the living tissue by heating the living tissue at a second temperature that is higher than the first temperature is supplied to the end effector; calculate elapsed time as an index value for a temperature of the end effector, the elapsed time beginning at a time when the end effector reaches the second temperature; compare the index value and a threshold value to obtain a comparison result; determine a residual heat level of the end effector based on the comparison result; and perform, based on determined the residual heat level, at least one of the following: issuance of a warning from a notifying unit; or adjustment of electrical power supplied to the end effector.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, a mode (hereinafter, embodiment) to implement the present disclosure will be described with reference to the drawings. The embodiment described hereafter are not intended to limit the present disclosure. Furthermore, like reference symbols are assigned to like parts throughout the drawings.

Schematic Configuration of Treatment System

Figure 1:
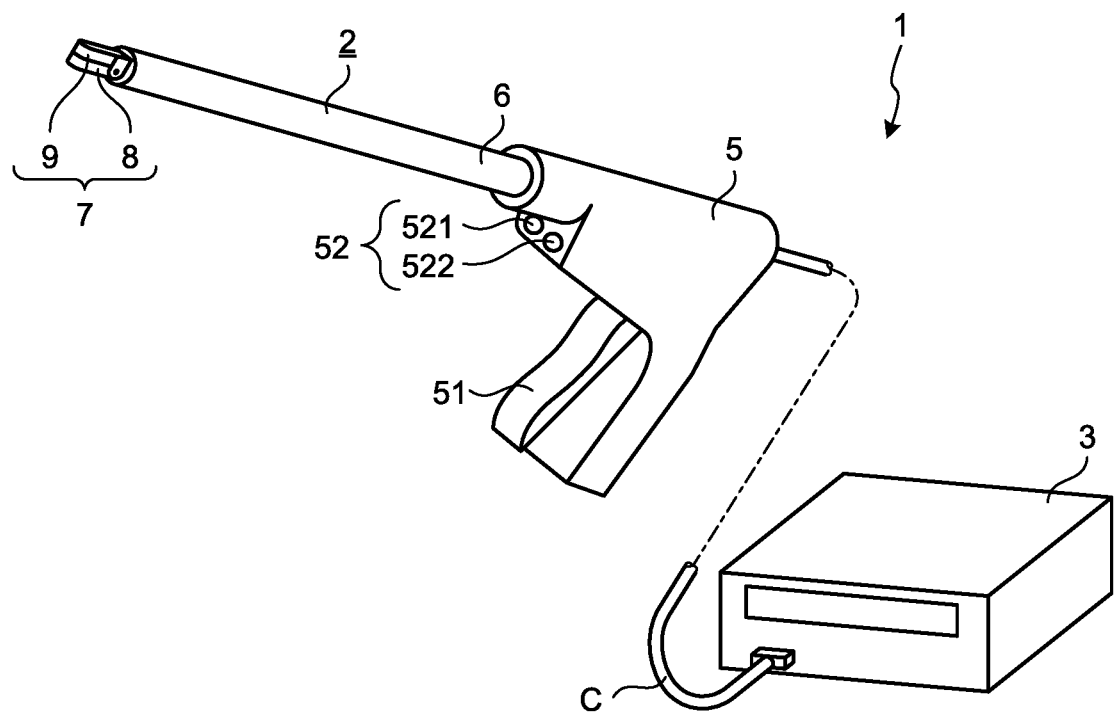
FIG. 1 illustrates a treatment system according to an embodiment.

FIG. 1 illustrates a treatment system 1 according to an embodiment.

The treatment system 1 corresponds to a medical device according to present disclosure. This treatment system 1 applies a treatment energy to a portion to be treated (hereinafter, denoted as target portion) in a living tissue, to thereby treat the target portion. In the present embodiment, a high frequency energy and a heat energy are used as the treatment energy. Moreover, treatments enabled by the treatment system 1 are two treatments including a first treatment to perform incision of a target portion, and a second treatment to perform sealing of a target portion.

This treatment system 1 includes a treatment tool 2 and a control device 3 as illustrated in FIG. 1.

Configuration of Treatment Tool

The treatment tool 2 is a surgical treatment tool to treat a target portion, for example, through an abdominal wall. This treatment tool 2 includes a handle 5, a shaft 6, and a grasping portion 7 as illustrated in FIG. 1.

Figure 5:
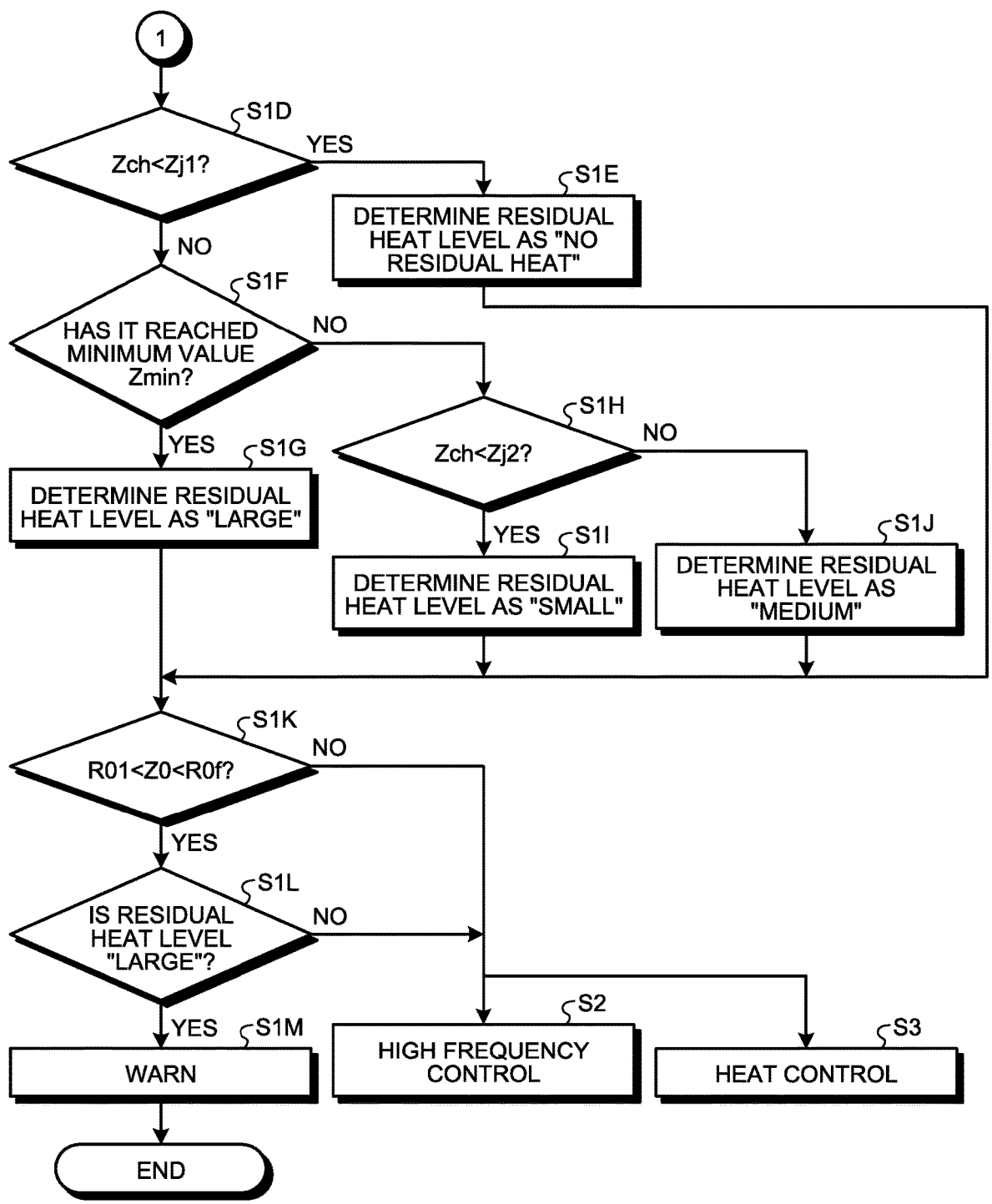
FIG. 5 is a flowchart of the residual-heat determining method.

The handle 5 is a portion held by a hand of an operator. In this handle 5, an operating knob 51 and an interface 52 are provided as illustrated in FIG. 5.

The interface 52 is arranged in a state exposed externally from the handle 5, and accepts a setting operation of an incision control mode and a sealing control mode. This interface 52 includes a first and a second switches 521, 522 as illustrated in FIG. 1.

The first switch 521 accepts a setting operation of the incision control mode input by the operator. The first switch 521 outputs an operation signal according to the setting operation to the control device 3, through an electric cable C (FIG. 1).

The second switch 522 accepts a setting operation of the sealing control mode input by the operator. The second switch 522 outputs an operation signal according to the setting operation to the control device 3 through the electric cable C.

The shaft 6 has a substantially cylindrical shape, and is connected to the handle 5 at its one end (FIG. 1). Moreover, at the other end of the shaft 6, the grasping portion 7 is attached. Inside this shaft 6, an opening and closing mechanism (not illustrated) that opens and closes a first and a second grasping members 8, 9 (FIG. 1) that constitute the grasping portion 7, according to an operation by the operator made with respect to the operating knob 51 is arranged. Furthermore, inside this shaft 6, the electric cable C (FIG. 1) is arranged from one end to the other end through the handle 5.

Configuration of Grasping Portion

Note that "distal end side" described hereafter is a distal end side of the grasping portion 7, and indicates a left side in FIG. 1. Moreover, "proximal end side" described hereafter signifies the shaft 6 side of the grasping portion 7, and indicates a right side in FIG. 1.

Figure 2:
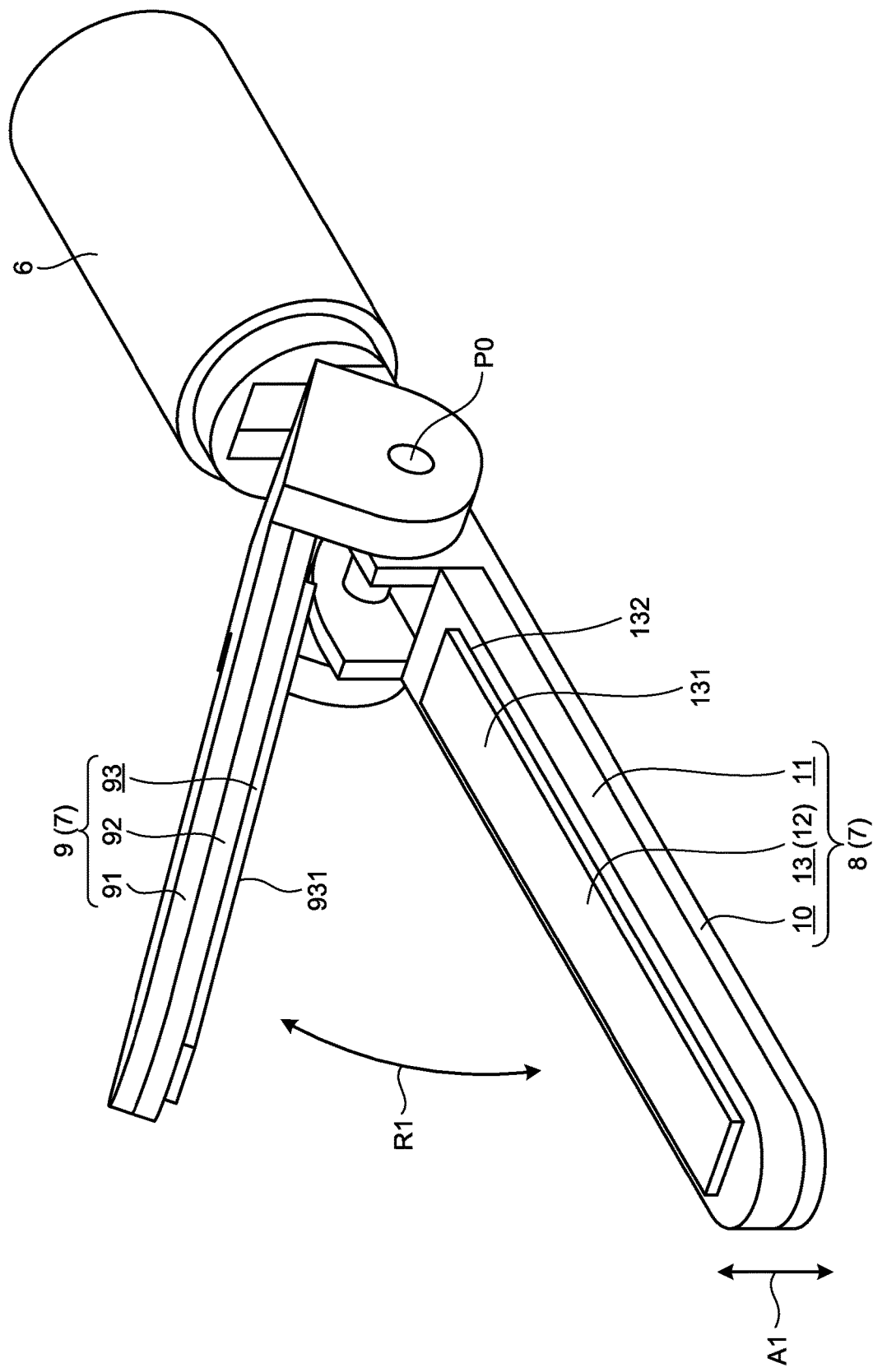
FIG. 2 illustrates a grasping portion.

FIG. 2 illustrates the grasping portion 7.

The grasping portion is a portion to treat a target portion in a state of grasping the target portion, and corresponds to the end effector according to the present invention. This grasping portion 7 includes the first and the second grasping members 8, 9 as illustrated in FIG. 1 or FIG. 2.

The first and the second grasping members 8, 9 are configured to be able to open and close in a direction of an arrow R1 (FIG. 2) according to an operation by the operator with respect to the operating knob 51.

Configuration of First Grasping Member

The first grasping member 8 is arranged at a position opposing to the second grasping member 9. This first grasping member 8 includes a first jaw 10, a first supporting member 11, and a treating portion 12 as illustrated in FIG. 2.

The first jaw 10 is a portion formed by extending a part of the shaft 6 toward the distal end side, and is formed in a long shape extending in a direction of length from a distal end to a proximal end of the grasping portion 7. This first jaw 10 is made from, for example, a metal material, such as stainless and titanium. The first jaw 10 supports the first supporting member 11 and the treating portion 12.

The first supporting member 11 has a long plate extending in a direction of length of the grasping portion 7, and is made from, for example, a resin material having a low thermal conductivity, such as polyetheretherketone (PEEK). This first supporting member 11 is arranged between the first jaw 10 and the treating portion 12.

The treating portion 12 generates a high frequency energy and a heat energy under control of the control device 3. This treating portion 12 includes a heat transfer plate 13 and a heater 14 (refer to FIG. 3) as illustrated in FIG. 2.

The heat transfer plate 13 is a flat board extending in a direction of length of the grasping portion 7, and is made from, for example, a conductive material, such as copper.

In this heat transfer plate 13, a surface on a direction of the second grasping member 9 is in contact with a target portion in a state in which the target portion is held by the first and the second grasping members 8, 9. The surface transfers heat from the heater 14 to the target portion. That is, the surface functions as a holding surface 131 (FIG. 2) that applies a heat energy to the target portion. In the present embodiment, the first holding surface 131 is constituted of a flat plane perpendicular to a direction A1 (FIG. 2) in which the first and the second grasping members 8, 9 oppose to each other in a state in which the first and the second grasping members 8, 9 hold the target portion. Moreover, in the heat transfer plate 13, a rear surface 132 that is on the back of the first holding surface 131 is similarly constituted of a flat plane perpendicular to the direction A1.

Furthermore, to the heat transfer plate 13, a pair of high frequency leads C1, C1' (refer to FIG. 3) constituting the electric cable C are connected.

The first holding surface 131 and the rear surface 132 are respectively constituted of flat planes, but it is not limited thereto, and may be formed respectively in other shaped, such as a convex shape and a concave shape. The same applies to a second holding surface 931 described later.

The heater 14 is, for example, a sheet heater, and is arranged on the rear surface 132 of the heat transfer plate 13. This heater 14 is formed, although specific illustration is omitted, by forming an electrical resistance pattern on a sheet-shaped substrate that is made from an insulating material, such as polyimide, by vapor deposition, or the like.

The electrical resistance pattern is formed along a U-shape following an outer edge shape of the heater 14. Moreover, to both ends of the electrical resistance pattern, a pair of heat generation leads C2, C2' (refer to FIG. 3) constituting the electric cable C are connected. Furthermore, to the electrical resistance pattern, an electric power is supplied through the pair of heat generation leads C2, C2', under control of the control device 3. Thus, the electrical resistance pattern generates heat.

Configuration of Second Grasping Member

The second grasping member 9 includes a second jaw 91, a second supporting member 92, and a counter plate 93 as illustrated in FIG. 2.

The second jaw 91 has a long shape extending in a direction of length of the grasping portion 7. In the second jaw 91, a proximal portion is pivotably supported about a fulcrum P0 (FIG. 2) with respect to the shaft 6, and opens and closes relative to the first grasping member 8 as it pivots.

The present embodiment adopts a structure in which the first grasping member 8 (the first jaw 10) is fixed to the shaft 6 and the second grasping member 9 (the second jaw 91) pivotably supported on the shaft 6, but it is not limited thereto. For example, a structure in which both the first and the second grasping members 8, 9 are pivotably supported on the shaft 6, and the first and the second grasping members 8, 9 open and close as they pivot may be adopted. Furthermore, for example, a structure in which the first grasping member 8 is pivotably supported on the shaft 6, the second grasping member 9 is fixed to the shaft 6, and it opens and closes relative to the second grasping member 9 as the first grasping member 8 pivots may be adopted.

The second supporting member 92 is made from a resin material having a low thermal conductivity, such as PEEK, and is arranged between the second jaw 91 and the counter plate 93.

The counter plate 93 is made from a conductive material, such as copper, and is fixed on a surface opposing to the first grasping member 8 in the second supporting member 92.

In this counter plate 93, a surface on the direction of the first grasping member 8 functions as the second holding surface 931 to hold a target portion with the first holding surface 131. Moreover, to the counter plate 93, the other high frequency lead C1' is connected.

Configuration of Control Device

Figure 3:
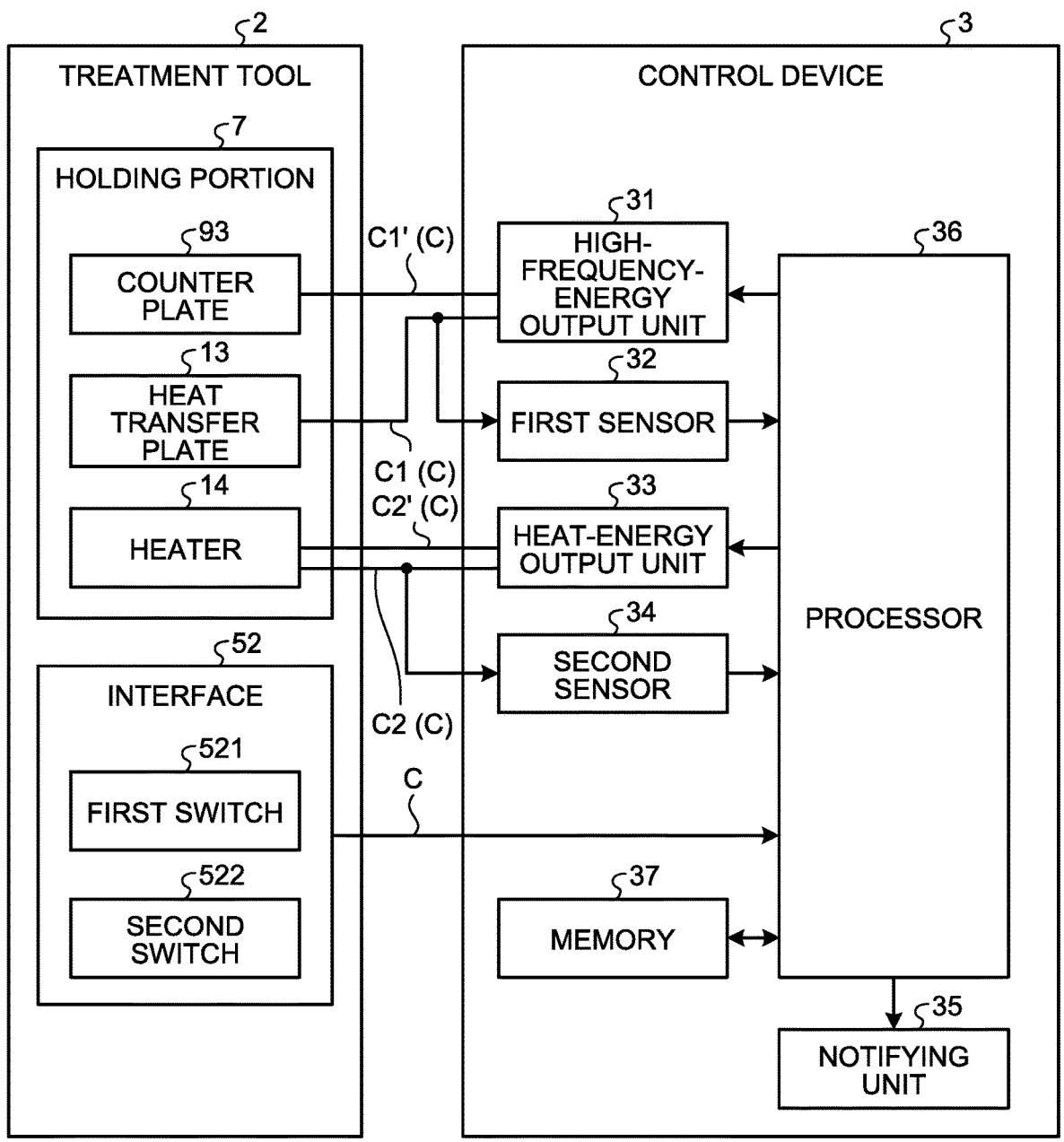
FIG. 3 is a block diagram illustrating a configuration of a control device.

FIG. 3 is a block diagram illustrating a configuration of the control device 3.

The control device 3 controls actions of the treatment tool 2 through the electric cable C in a centralized manner. This control device 3 includes a high-frequency-energy output unit 31, a first sensor 32, a heat-energy output unit 33, a second sensor 34, an notifying unit 35, a processor 36, and a memory 37 as illustrated in FIG. 3.

The high-frequency-energy output unit (generator)31 supplies a high frequency electric power to the heat transfer plate 13 and the counter plate 93 through one pair of the high frequency leads C1, C1', under control of the processor 36. Thus, the high frequency electric current flows through a target portion held between the heat transfer plate 13 and the counter plate 93. In other words, to the target portion held between the heat transfer plate 13 and the counter plate 93, a high frequency energy is applied. That is, the heat transfer plate 13 and the counter plate 93 respectively function as high frequency electrodes according to the present disclosure.

The first sensor 32 detects a voltage value and an current value supplied to the heat transfer plate 13 and the counter plate 93 from the high-frequency-energy output unit 31. The first sensor 32 then outputs a signal according to the detected voltage value and current value to the processor 36.

The heat-energy output unit (generator) 33 supplies an electric power to the electrical resistance pattern constituting the heater 14 through one pair of the heat generation leads C2, C2', under control of the processor 36. Thus, the electrical resistance pattern generates heat. To the target portion held between the heat transfer plate 13 and the counter plate 93, the heat of the electrical resistance pattern is transferred from the heat transfer plate 13. In other words, a heat energy is applied to the target portion held between the heat transfer plate 13 and the counter plate 93.

The second sensor 34 detects a voltage value and an current value supplied to the heater 14 from the heat-energy output unit 33. The second sensor 34 then outputs a signal according to the detected voltage value and current value to the processor 36.

The notifying unit 35 notifies of predetermined information under control of the processor 36. Examples of this notifying unit 35 includes, for example, a light emitting diode (LED) that notifies of predetermined information depending on lighting, flashing, or a color when it is lit, a display device that displays predetermined information, and a speaker that outputs predetermined information by sound.

The processor 36 is, for example, a central processing unit (CPU), a field programmable gate array (FPGA), or the like, and controls overall actions of the treatment system 1 in accordance with a program stored in the memory 37. Detailed functions of the processor 36 will be described in "Control Method Performed by Processor" later.

The memory 37 stores a program (including a residual-heat determining program according to the present disclosure) executed by the processor 36, information necessary for processing of the processor 36, and the like.

Control Method Performed by Processor

Next, a control method performed by the processor 36 will be explained.

In the following, as the control method performed by the processor 36, a residual-heat determining method, a high frequency control, and a heat control will be explained sequentially.

Residual-Heat Determining Method

First, the residual-heat determining method performed by the processor 36 will be explained.

Figure 4:
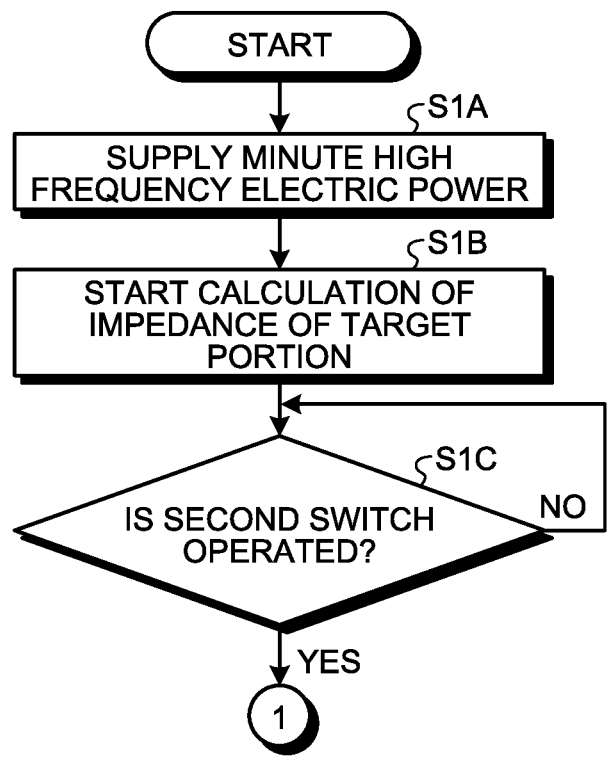
FIG. 4 is a flowchart of a residual-heat determining method.
Figure 6:
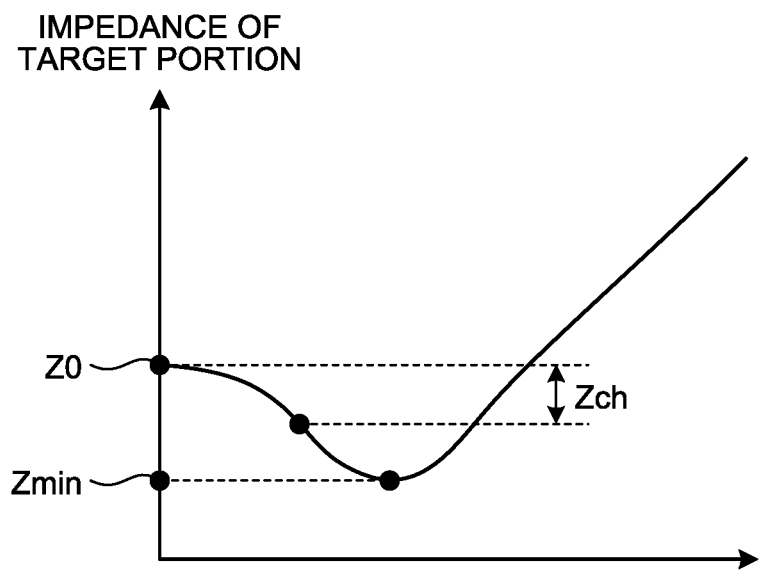
FIG. 6 shows a behavior of impedance of a target portion when the residual-heat determining method is performed.
Figure 7:
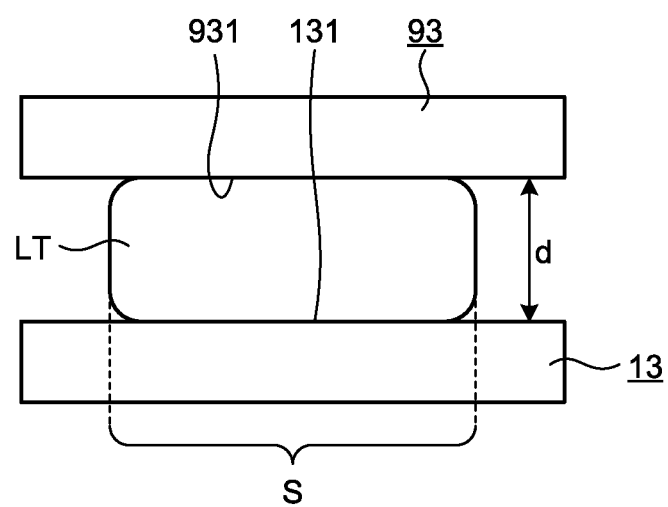
FIG. 7 is a diagram for explaining a determining method of a type of a target portion.
Figure 8:
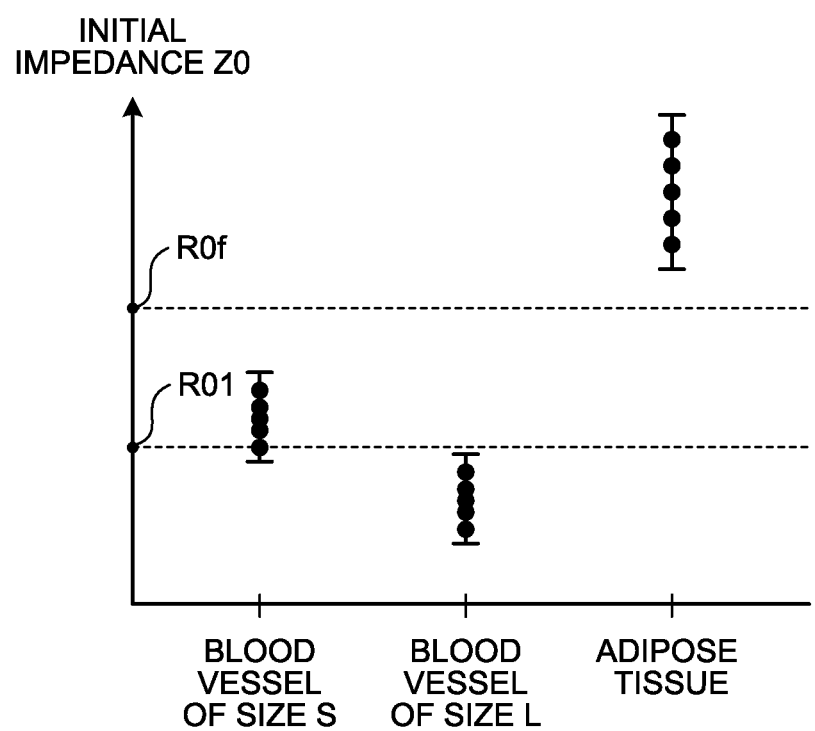
FIG. 8 is a diagram for explaining a determining method of a type of a target portion.

FIG. 4 and FIG. 5 are flowcharts of the residual-heat determining method. FIG. 6 shows a behavior of impedance of a target portion when the residual-heat determining method is performed. FIG. 7 and FIG. 8 are diagrams for explaining a determining method of a type of a target portion LT. Specifically, FIG. 7 schematically illustrates a state in which the target portion LT is held by the heat transfer plate 13 and the counter plate 93. FIG. 8 shows distributions of an initial impedance Z0 of a small blood vessel of size S, a large blood vessel of size L, and the initial impedance Z0 in an adipose tissue, respectively.

An operator holds the treatment tool 2 with a hand, and inserts a distal end portion of the treatment tool 2 (the grasping portion 7 and a part of the shaft 6) into an abdominal cavity through an abdominal wall by using a trocar, or the like. Furthermore, the operator holds the target portion LT (FIG. 7) with the grasping portion 7 by operating the operating knob 51. In this state, the processor 36 supplies a minute high frequency electric power to the heat transfer plate 13 and the counter plate 93 from the high-frequency-energy output unit 31 through one pair of the high frequency leads C1, C1' (step S1A). Thus, a detection current flows to the target portion LT held between the heat transfer plate 13 and the counter plate 93.

The minute high frequency electric power signifies an electric power so small not to cause thermal denaturation in the target portion LT held between the heat transfer plate 13 and the counter plate 93.

After step S1A, the processor 36 starts calculation of an impedance of the target portion LT based on a voltage value and a current value detected by the first sensor 32 (step S1B). The processor 36 stores calculated impedances of the target portion LT sequentially in the memory 37. The impedance of the target portion LT corresponds to an index value and a thermal denaturation level according to the present disclosure. That is, the processor 36 calculates the index value according to the present disclosure before application of a high frequency energy to the target portion LT (step S2E) described later, and application of a heat energy to the target portion LT (step S3B) described later.

In the following, an impedance of the target portion LT calculated first, that is, an impedance that is stored in the memory 37 first, is referred to as the initial impedance Z0 (FIG. 6), for convenience of explanation. Furthermore, calculation of an impedance of the target portion LT and storage into the memory 37 are continued also in a first and a second phases described later.

After step S1B, the processor 36 monitors whether the setting operation of the sealing control mode is performed by the operator with respect to the second switch 522 all the time (step S1C).

The processor 36 performs following processing when the setting operation of the incision control mode is performed by the operator with respect to the first switch 521.

The processor 36 activates both the high-frequency-energy output unit 31 and the heat-energy output unit 33 to incise the target portion LT. The high-frequency-energy output unit 31 supplies relatively high energy high frequency electric power to the heat transfer plate 13 and the counter plate 93 through one pair of the high frequency leads C1, C1'. Moreover, the heat-energy output unit 33 supplies relatively high energy electric power to the electrical resistance pattern constituting the heater 14 through one pair of the heat generation leads C2, C2'. Thus, the temperature of the heat transfer plate 13 and the counter plate 93 increases to a second temperature of, for example, approximately 300° C. that enables incision of the target portion LT. Furthermore, as time passes from a point of time when execution of the incision control mode is finished, the temperature of the heat transfer plate 13 and the counter plate 93 decreases.

When residual heat is not remained in the heat transfer plate 13 and the counter plate 93, the impedance of the target portion LT does not change from the initial impedance Z0 only by holding the target portion LT.

On the other hand, when residual heat is remained in the heat transfer plate 13 and the counter plate 93, the target portion LT is denatured by the residual heat. That is, the impedance of the target portion LT gradually decreases as illustrated in FIG. 6 because of the residual heat. Moreover, when the residual heat is relatively large, the impedance of the target portion LT turns to increase after it reaches the minimum value Zmin.

That is, it becomes possible to determine a residual heat level based on an amount of change Zch (FIG. 6) from the initial impedance Z0.

When a setting operation of the sealing control mode is performed by the operator with respect to the second switch 522 (step S1C: YES), the processor 36 executes the sealing control mode.

First, the processor 36 reads a latest impedance and the initial impedance Z0 out of plural impedances of the target portion LT stored in the memory 37. The processor 36 then determines whether the amount of change Zch from the initial impedance Z0 to the latest impedance is smaller than a residual-heat determination threshold Zj1 (step S1D).

When it is determined that the amount of change Zch is smaller than the residual-heat determination threshold Zj1 (step S1D: YES), the processor 36 determines the residual heat level of the heat transfer plate 13 and the counter plate 93 as "no residual heat" (step S1E). The processor 36 then stores the determination result in the memory 37. Thereafter, the processor 36 shifts to step S1K.

On the other hand, when it is determined that the amount of change Zch is equal to or larger than the residual-heat determination threshold Zj1 (step S1D: NO), the processor refers to plural impedances of the target portion LT stored in the memory 37, and determines whether the impedance of the target portion LT has reached the minimum value Zmin (step S1F).

When it is determined that the impedance of the target portion LT has reached the minimum value Zmin (step S1F: YES), the processor 36 determines the residual heat level of the heat transfer plate 13 and the counter plate 93 as "large" (step S1G). The processor 36 then stores the determination result in the memory 37. Thereafter, the processor 36 shifts to step S1K.

On the other hand, when it is determined that the impedance of the target portion LT has not reached the minimum value Vmin (step S1F: NO), the processor 36 determines whether the amount of change Zch is smaller than a residual-heat determination threshold Zj2 (step S1H). The residual-heat determination threshold Zj2 is a value larger than the residual-heat determination threshold Zj1.

When it is determined that the amount of change Zch is smaller than the residual-heat determination threshold Zj2 (step S1H: YES), the processor 36 determines the residual heat level of the heat transfer plate 13 and the counter plate 93 as "small" (step S1I). The processor 36 then stores the determination result in the memory 37. Thereafter, the processor 36 shifts to step S1K.

On the other hand, when it is determined that the amount of change Zch is equal to or larger than the residual-heat determination threshold Zj2 (step S1H: NO), the processor 36 determines the residual heat level of the heat transfer plate 13 and the counter plate 93 as "medium" (step S1J). The processor 36 then stores the determination result in the memory 37. Thereafter, the processor 36 shifts to step S1K.

As described above, after the setting operation of the sealing control mode with respect to the second switch 522 (step S1C: YES), the processor performs determination of a residual heat level (steps S1E, S1G, S1I, S1J). That is, the processor 36 performs determination of a residual heat level (steps S1E, S1G, S1I, S1J) before application of a high frequency energy to the target portion LT (step S2E) described later and application of a heat energy to the target portion LT (step S3B) described later.

The initial impedance Z0 of the target portion LT is determined by following Equation (1). In Equation (1), p is a resistivity of the target portion LT. S is a cross-sectional area of the target portion LT as illustrated in FIG. 7. d is a thickness of the target portion LT.

$$Z0 = \rho \frac{d}{S} \quad (1)$$

Because the resistivity p is larger when the target portion LT is an adipose tissue, the initial impedance Z0 is to be large. Moreover, when the target portion Lt is a blood vessel tissue, the resistivity p is to be uniform regardless of a size of the blood vessel tissue. Furthermore, because it is held by the heat transfer plate 13 and the counter plate 93, the thickness d is to be uniform also. However, as the size of the blood vessel tissue increases, the cross-sectional area S increases and, therefore, the initial impedance Z0 becomes small.

That is, when the initial impedance Z0 is larger than a discrimination threshold R0f (FIG. 8), it is possible to determine whether the target portion LT is an adipose tissue or a blood vessel tissue. However, although there is a tendency that the initial impedance Z0 decreases as the size of the blood vessel tissue increases, it is impossible to determine the size of a blood vessel tissue even by using the initial impedance Z0 because distributions of the initial impedance Z0 of the blood vessel of size S and the blood vessel of size L overlap each other as illustrated in FIG. 8. Note that if a discrimination threshold R01 (FIG. 8) larger than a distribution of the initial impedance Z0 of the blood vessel of size L is used, the target portion LT having the initial impedance Z0 larger than the discrimination threshold R01 and smaller than the discrimination threshold R0f can be determined as a blood vessel of size S obviously.

The processor 36 then performs step S1K described below.

The processor 36 reads the initial impedance Z0 stored in the memory 37. The processor 36 then determines whether the read initial impedance Z0 is larger than the discrimination threshold R01 and smaller than the discrimination threshold R0f; that is, whether the target portion LT is a blood vessel of size S.

When it is determined that the target portion LT is not a blood vessel of size S (step S1K: NO), the processor 36 starts the high frequency control and the heat control at steps S2, S3.

On the other hand, when it is determined that the target portion LT is a blood vessel of size S (step S1K: YES), the processor 36 refers to a determination result of a residual heat level stored in the memory 37, and determines whether the residual heat level of the heat transfer plate 13 and the counter plate 93 is "large" based on the determination result (step S1L).

When it is determined that the residual heat level is not "large" (step S1L: NO), the processor 36 starts the high frequency control and the heat control at steps S2, S3.

On the other hand, it is determined that the residual heat level is "large" (step S1L: YES), the processor 36 causes the notifying unit 35 to notify of information indicating a warning (step S1M). That is, the processor 36 causes the notifying unit 35 to notify of information indicating a warning when the residual heat level exceeds a specific level. The processor 36 then ends this control flow. That is, the processor 36 does not perform the high frequency control and the heat control (steps S2, S3) when the residual heat level exceeds a specific level by inhibiting supply of electric power to the holding portion 7. Thus, it is possible to appropriately avoid a blood vessel of size S, which is particularly sensitive to temperature, from being excessively heated.

High Frequency Control

Next, the high frequency control (step S2) performed by the processor 36 will be explained. The high frequency control (step S2) is divided into a first and a second phases. In the following, the first and the second phases are sequentially explained as the high frequency control (step S2).

First Phase

Figure 9:
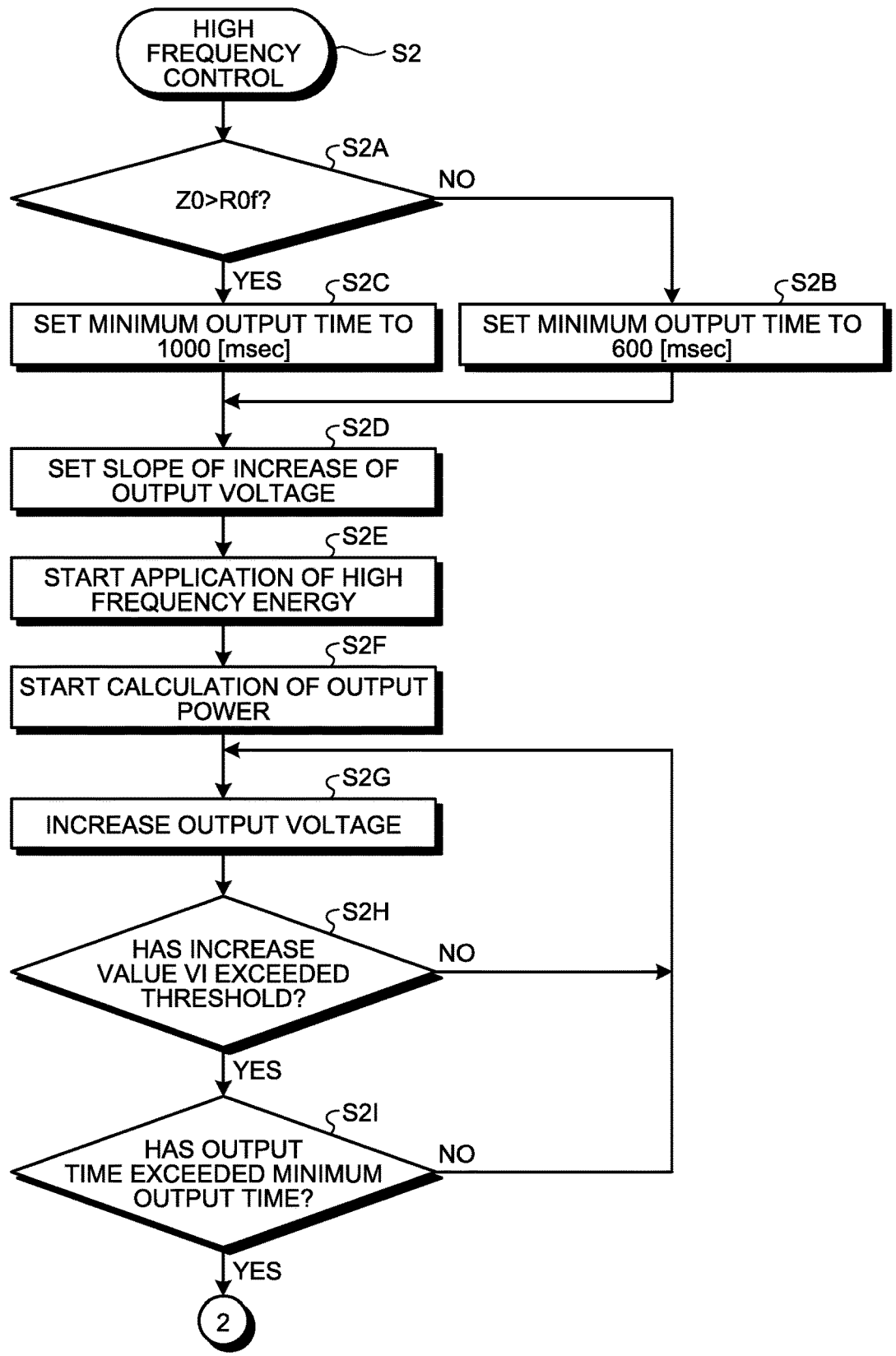
FIG. 9 is a flowchart showing a first phase of a high frequency control.
Figure 10:
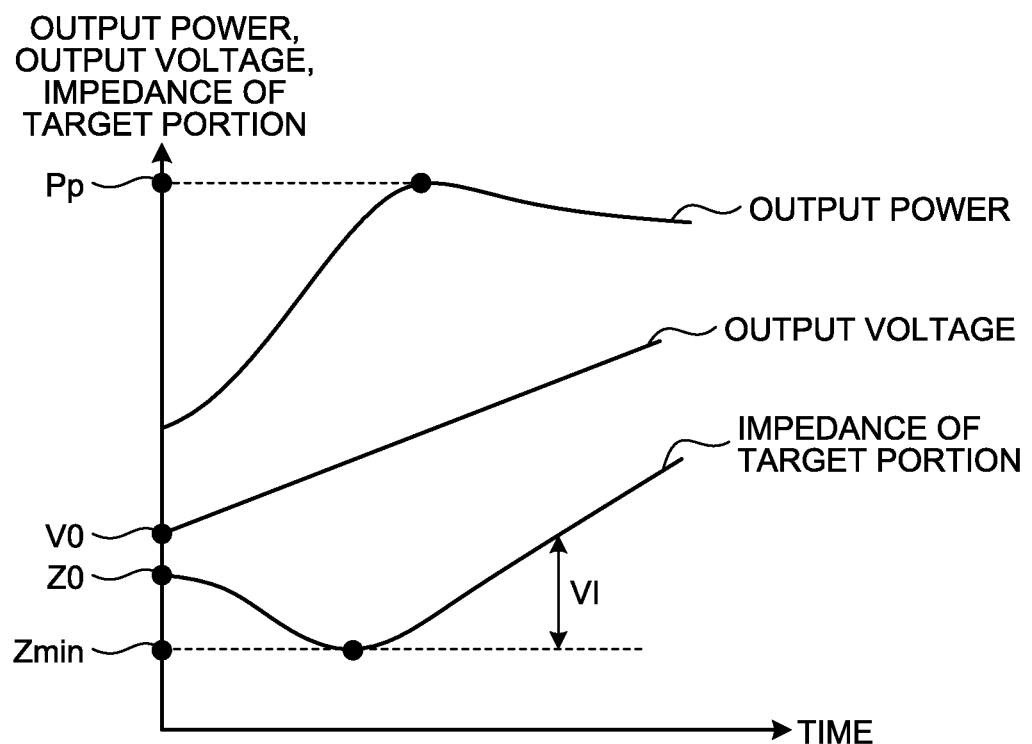
FIG. 10 shows an output power, an output voltage, and a behavior of impedance of a living tissue when the first phase is performed.

FIG. 9 is a flowchart showing a first phase of the high frequency control. FIG. 10 shows an output power, an output voltage, and a behavior of impedance of the target portion LT when the first phase is performed. For convenience of explanation, FIG. 10 shows an output power, an output voltage, and a behavior of impedance of the target portion LT when the residual heat level of the heat transfer plate 13 and the counter plate 93 is "no residual heat".

The first phase is a phase in which the target portion LT is uniformly heated by starting supply of an output voltage to the heat transfer plate 13 and the counter plate 93 from the high-frequency-energy output unit 31, and by raising the output voltage.

First, the processor 36 reads the initial impedance Z0 stored in the memory 37. The processor 36 then determines whether the read initial impedance Z0 is larger than the discrimination threshold R0f, that is, whether the target portion LT is an adipose tissue (step S2A).

When it is determined that the target portion LT is not an adipose tissue (step S2A: NO, the processor 36 sets a minimum output time to apply the high frequency energy to the target portion LT in the first phase to 600 [msec] (step S2B). Thereafter, the processor 36 shifts to step S2D.

On the other hand, when it is determined that the target portion LT is an adipose tissue (step S2A: YES), the processor 36 sets the minimum output time to apply the high frequency energy to the target portion LT in the first phase to 1000 [msec] (step S2C). Thereafter, the processor 36 shifts to step S2D.

At steps S2B, S2C, the minimum output time is not limited to the time described above as long as the minimum output time set at step S2C is larger than the minimum output time set at step S2B.

The processor 36 performs step S2D described below.

The processor 36 sets a slope of increase of the output voltage to be supplied to the heat transfer plate 13 and the counter plate 93 from the high-frequency-energy output unit 31 in the first phase.

In the first phase, if the output voltage to be supplied to the heat transfer plate 13 and the counter plate 93 from the high-frequency-energy output unit 31 is suddenly increased, the temperature of the target portion LT abruptly increases. That is, the target portion LT cannot be heated uniformly. Temperature unevenness in the target portion LT deteriorates a sealing performance of the target portion LT.

Accordingly, the processor 36 sets the slope of increase of the output voltage so as to be proportional respectively to an inverse of the initial impedance Z0 and an inverse of the residual heat level, based on the initial impedance Z0 and the determination result of the residual heat level stored in the memory 37 at step S2D. That is, because the smaller the target portion LT is, the more sensitive it is to temperature, the processor 36 sets the slope of increase of the output voltage to be gentler for the smaller target portion LT. Although the size of a blood vessel tissue cannot be identified only with the initial impedance Z0, it is also true that the initial impedance Z0 of a blood vessel of size S is larger than that of a blood vessel of size L (FIG. 8). Therefore, the processor 36 sets the slope of increase of the output voltage to be gentler as the initial impedance Z0 increases to be larger. Moreover, the higher the residual heat of heat transfer plate 13 and the counter plate 93 is, the gentler, the slope of increase of the output voltage is set to by the processor 36, to avoid sudden temperature rise of the target portion LT caused by the residual heat of the heat transfer plate 13 and the counter plate 93. That is, the processor 36 reduces a power to be supplied to the heat transfer plate 13 and the counter plate 93 to be less as the residual heat level increases. Furthermore, the processor 36 adjusts a power to be supply to the heat transfer plate 13 and the counter plate 93 based on a determination result of the residual heat level in the sealing control mode. The slope of increase of the output voltage corresponds to a control target value according to the present disclosure. That is, the processor 36 changes the control target value according to the present disclosure based on a determination result of the residual heat level.

After step S2D, the processor 36 starts supply of the output voltage to the heat transfer plate 13 and the counter plate 93 from the high-frequency-energy output unit (step S2E). That is, application of the high frequency energy to the target portion LT is started. The output voltage to be supplied at the time of start does not vary depending on a type and a size of the target portion LT, but is all uniformly an initial voltage V0 (FIG. 10). Thus, the high frequency current flows through the target portion LT, and the target portion LT is heated.

After step S2E, the processor 36 starts calculation of the output voltage being supplied to the heat transfer plate 13 and the counter plate 93 from the high-frequency-energy output unit 31 based on a voltage value and a current value detected by the first sensor 32 (step S2F). The processor 36 then stores the calculated output power sequentially in the memory 37.

After step S2F, the processor 36 refers to the slope of increase of the output voltage set at step S2D, and increases the output voltage to be supplied to the heat transfer plate 13 and the counter plate 93 from the high-frequency-energy output unit 31 as shown in FIG. 10 (step S2G).

A behavior of impedance of the target portion LT after the application of the high frequency energy is started (step S2E) is as shown in FIG. 10.

Specifically, the impedance of the target portion LT decreases as the target portion LT is heated, and takes the minimum value Zmin when moisture in the target portion LT becomes a boiling state. Moreover, the impedance of the target portion LT turns to increase when application of heat to the target portion LT is further continued because the moisture in the target portion LT evaporates.

That is, when an increase value VI (FIG. 10) of the impedance of the target portion LT exceeds a predetermined threshold from the minimum value Zmin, it can be determined that it has shifted from a heated state to a dry state.

After step S2G, the processor 36 reads the minimum value Zmin and a latest impedance out of plural impedances of the target portion LT stored in the memory 37. The processor 36 determines whether the increase value VI from the minimum value Zmin to the latest impedance has exceeded the predetermined threshold (step S2H).

When it is determined that the increase value VI has not exceeded the predetermined threshold (step S2H: NO), the processor 36 returns to step S2G.

On the other hand, when it is determined that the increase value VI has exceeded the predetermined threshold (step S2H: YES), the processor 36 determines whether elapsed time since the application of the high frequency energy is started (step S2E) has exceeded the minimum output time set at steps S2B, S2C (step S2I).

When it is determined that the elapsed time has not exceeded the minimum output time (step S2I: NO), the processor 36 returns to step S2G.

On the other hand, when it is determined that the elapsed time has exceeded the minimum output time (step S2I: YES), the processor 36 finishes the first phase, and shifts to the second phase.

Second Phase

Figure 11:
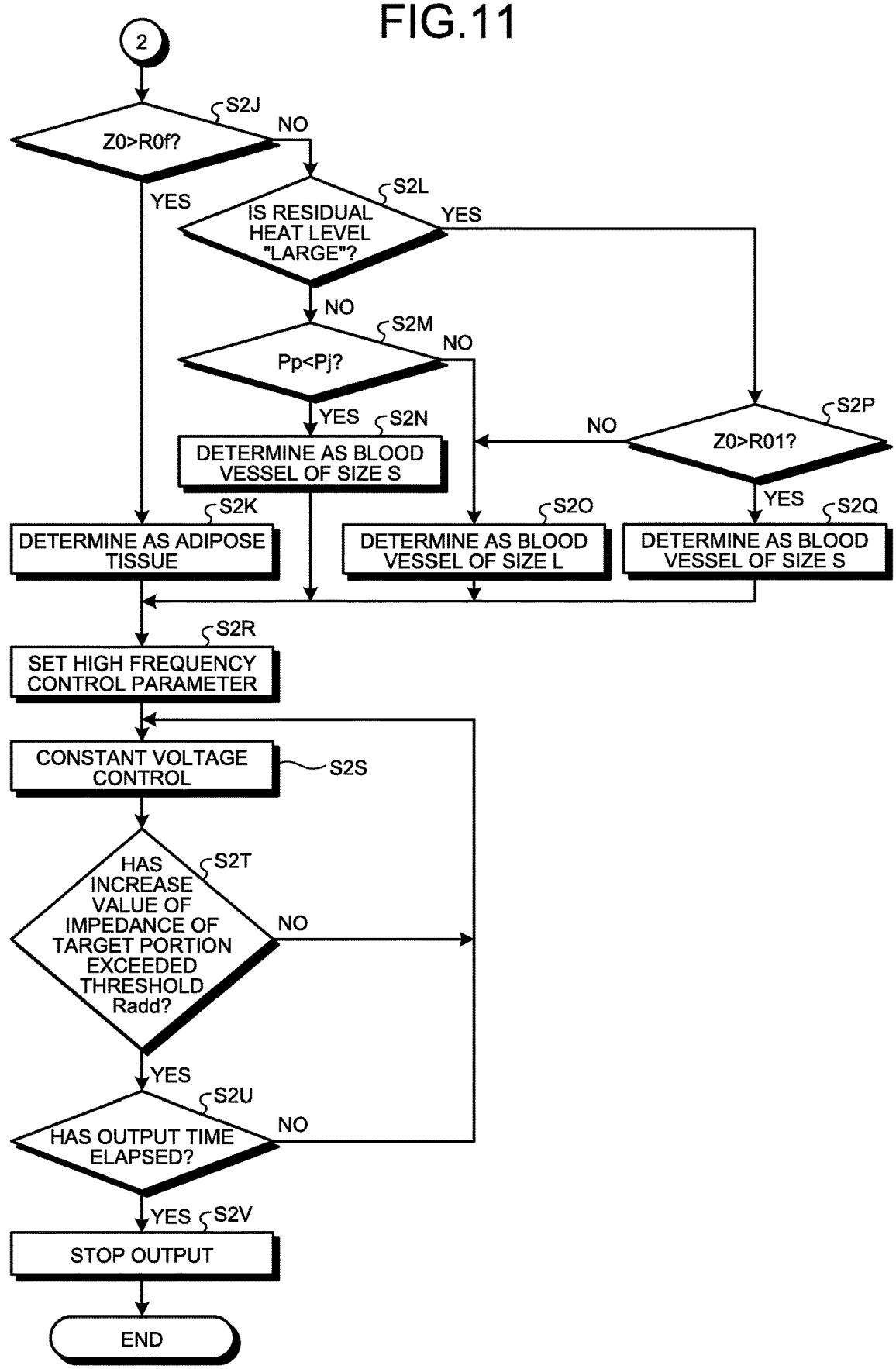
FIG. 11 is a flowchart showing a second phase of the high frequency control.
Figure 12:
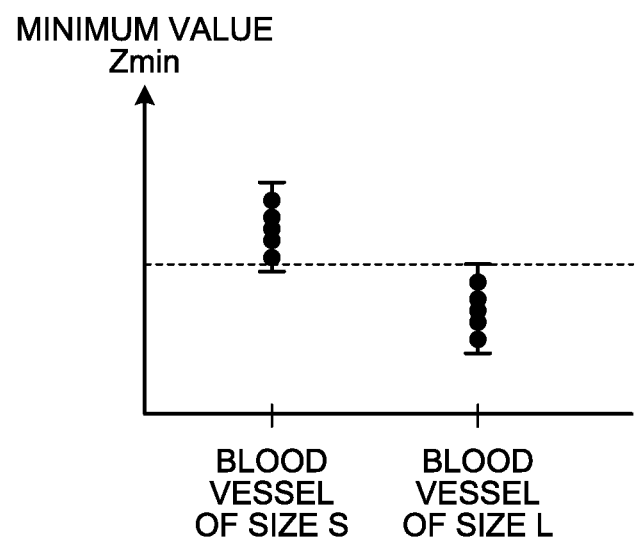
FIG. 12 is a diagram for explaining a determining method of a size of a target portion.
Figure 13:
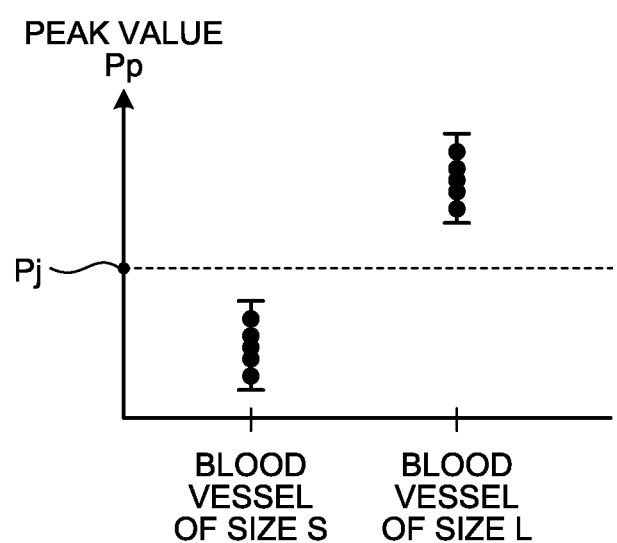
FIG. 13 is a diagram for explaining a determining method of a size of a target portion.

FIG. 11 is a flowchart showing the second phase of the high frequency control. FIG. 12 and FIG. 13 are diagrams for explaining a determining method of a size of the target portion LT. Specifically, FIG. 12 is a diagram respectively showing distributions of the minimum value Zmin of a blood vessel of size S and a blood vessel of size L. FIG. 13 is a diagram showing distributions of a peak value Pp of an output power of the blood vessel of size S and the blood vessel of size L.

The second phase is a phase in which the target portion LT is exsiccated to a deep portion by controlling the output voltage to be supplied to the heat transfer plate 13 and the counter plate 93 from the high-frequency-energy output unit 31 to be uniform.

First, the processor 36 reads the initial impedance Z0 stored in the memory 37. The processor 36 then determines whether the read initial impedance Z0 is larger than the discrimination threshold R0f (step S2J).

When it is determined that the initial impedance Z0 is larger than the discrimination threshold R0f (step S2J: YES), the processor 36 determines that the target portion LT is an adipose tissue (step S2K). The processor 36 stores the determination result (hereinafter, described as tissue discrimination result) in the memory 37. Thereafter, the processor 36 shifts to step S2R.

On the other hand, when it is determined that the initial impedance Z0 is equal to or smaller than the discrimination threshold R0f (step S2J: NO), the processor 36 refers to the residual heat level stored in the memory 37, and determines whether the residual heat level of the heat transfer plate 13 and the counter plate 93 is "large" based on the determination result (step S2L).

As described above, it is impossible to discriminate a blood vessel of size S from a blood vessel of size L with the initial impedance value Z0. Moreover, as for the minimum value Zmin also, although there is a tendency that the minimum value Zmin decreases as the size of the blood vessel tissue increases, it is impossible to discriminate a blood vessel of size S from a blood vessel of size L with the initial impedance Z0 because distributions of the minimum value Zmin of the blood vessel of size S and the blood vessel of size L overlap each other as shown in FIG. 12.

It has been experimentally found that the size of a blood vessel tissue can be determined if the peak value Pp (FIG. 10) of an output power in the first phase is used. That is, as shown in FIG. 13, when the peak value Pp is smaller than a discrimination threshold Pj, it is possible to determine that the target portion LT is a blood vessel of size S. On the other hand, when the peak value Pp is equal to or larger than the discrimination threshold Pj, it is possible to determined that the target portion LT is a blood vessel of size L. The peak value Pp includes both information about the minimum value Zmin and time until it reaches the minimum value Zmin (amount of the output voltage). It is assumed that the reason why the peak value Pp enabled to determine the size of a blood vessel tissue is because it is information including not only an impedance in a boiling state (the minimum value Zmin), but also information of time until it reaches the boiling state, and the like.

When it is determined that the residual heat level is not "large" (step S2L: NO), the processor 36 reads the peak value Pp out of plural output values stored in the memory 37. The processor 36 then determines whether the read peak value Pp is smaller than the discrimination threshold Pj (step S2M).

When it is determined that the peak value Pp is smaller than the discrimination threshold Pj (step S2M: YES), the processor 36 determines that the target portion LT is a blood vessel of size S (step S2N). The processor 36 then stores the determination result (hereinafter, described as tissue determination result) in the memory 37. Thereafter, the processor 36 shifts to step S2R.

On the other hand, when it is determined that the peak value Pp is equal to or larger than the discrimination threshold Pj (step S2M: NO), the processor 36 determines that the target portion LT is a blood vessel of size L (step S2O). The processor 36 then stores the determination result (hereinafter, described as tissue determination result) in the memory 37. Thereafter, the processor 36 shifts to step S2R.

On the other hand, when it is determined that the residual heat level is "large" (step S2L: YES), the processor 36 reads the initial impedance Z0 out of plural impedances of the target portion LT stored in the memory 37. The processor 36 determines whether the read initial impedance Z0 is larger than the discrimination threshold R01 (step S2P).

When it is determined that the initial impedance Z0 is larger than the discrimination threshold R01 (step S2P: YES), the processor 36 determines that the target portion LT is a blood vessel of size S (step S2Q). The processor 36 then stores the determination result (hereinafter, described as tissue determination result) in the memory 37. Thereafter, the processor 36 shifts to step S2R.

On the other hand, when it is determined that the initial impedance Z0 is equal to or smaller than the discrimination threshold R01 (step S2P: NO), the processor shifts to step S2O, and determines that the target portion LT is a blood vessel of size L.

That is, the processor 36 determines the size of a blood vessel tissue by using the initial impedance Z0 not the peak value Pp when the residual heat level of the heat transfer plate 13 and the counter plate 93 is "large".

Although the sizes of a blood vessel tissue is determined by comparing the initial impedance Z0 with the discrimination threshold R01 at step S2P, it is not limited thereto. For example, the target portion LT may be determined as a blood vessel of size S when both a first condition that the initial impedance Z0 is larger than the discrimination threshold R01 and a second condition that the minimum value Zmin is larger than a predetermined threshold are both satisfied, and may be determined that the target portion LT is a blood vessel of size L when either of the first and the second conditions is not satisfied.

The processor 36 then performs step S2R described below.

The processor 36 refers to the determination result of the residual heat level and the tissue determination result stored in the memory 37, and first reference information that has been stored in advance in the memory 37, to set high frequency control parameters in the second phase. Examples of the first reference information includes information indicated in Table 1 below.

TABLE 1

| Tissue determination result | High frequency control parameter | Determination result of residual heat level | | | |
|---|---|---|---|---|---|
| | | No residual heat | Small | Medium | Large |
| Adipose tissue | Threshold Radd [Ω] | 300 | 300 | 300 | 290 |
| | Output time [msec] | 3000 | 2800 | 2700 | 2600 |
| | Output voltage [V] | 75 | 70 | 68 | 65 |
| Blood vessel of size L | Threshold Radd [Ω] | 300 | 300 | 300 | 290 |
| | Output time [msec] | 3000 | 2800 | 2700 | 2600 |
| | Output voltage [V] | 50 | 48 | 45 | 40 |
| Blood vessel of size S | Threshold Radd [Ω] | 150 | 150 | 150 | — |
| | Output time [msec] | 500 | 480 | 460 | — |
| | Output voltage [V] | 30 | 28 | 26 | — |

The first reference information is information in which a determination result of a residual heat level ("no residual heat", "small", "medium", and "large"), a tissue determination result ("adipose tissue", "blood vessel of size L", and "blood vessel of size S"), and a high frequency control parameters in the second phase are associated with one another as indicated in Table 1.

The high frequency control parameters in the second phase are three parameters including a thresholds Radd [Ω], output time [msec] in which a constant voltage control (step S2S) described later is performed, and an output voltage [V] as indicated in Table 1. The threshold Radd is a threshold compared with an increase value of impedance of the target portion LT since the constant voltage control (step S2S) described later is started. The output voltage [V] is set to take a smaller value as a determination result of a residual heat level shifts as "no residual heat", "small", "medium", and to "large", that is, as the residual heat level increases as indicated in Table 1. That is, the processor 36 reduces the power to be supplied to the heat transfer plate 13 and the counter plate 93 to be less as the residual heat level increases. Moreover, the processor 36 adjusts the power to be supplied to the heat transfer plate 13 and the counter plate 93 based on a determination result of a residual heat level in the sealing control mode. The high frequency control parameter corresponds to the control target value according to the present disclosure. That is, the processor 36 changes the control target value according to the present disclosure based on a determination result of a residual heat level. Moreover, when a determination result of a residual heat level is "large", and a tissue determination result is "blood vessel of size S", information indicating warning is notified at step S1M, and the high frequency energy is thus not applied to the target portion LT. Therefore, values of the three high frequency control parameters are not set.

Values of the threshold Radd, the output time, and the output voltage are not limited to values indicated in Table 1, but other values can be applied as long as they do not decrease as the determination result of a residual heat level shifts as "large", "medium", "small", and to "no residual heat", that is, as the residual heat level decreases, and as long as they do not increase as the tissue determination result shifts from "adipose tissue", "blood vessel of size L", and to "blood vessel of size S".

The processor 36 sets the threshold Radd to 290 [Ω], the output time to 2600 [msec], and the output voltage to 40 [V], for example, when the determination result of a residual heat level is "large", and the tissue determination result is "blood vessel of size L" at step S2R.

After step S2R, the processor 36 performs the constant voltage control to supply the output voltage set at step S2R to the heat transfer plate 13 and the counter plate 93 from the high-frequency-energy output unit 31 (step S2S).

After step S2S, the processor 36 reads an impedance at the time of start of the constant voltage control (step S2S) and a latest impedance out of plural impedances of the target portion LT stored in the memory 37. The processor 36 then determines whether an increase value from the impedance at the time of start to the latest impedance exceeds the threshold Radd set at step S2R (step S2T).

When it is determined that the increase value has not exceeded the threshold Radd (step S2T: NO), the processor 36 returns to step S2S, and continues the constant voltage control.

On the other hand, when it is determined that the increase value has exceeded the threshold Radd (step S2T: YES), the processor 36 determines whether elapsed time since the start of the constant voltage control (step S2S) has exceeded the output time set at step S2R (step S2U).

When it is determined that the elapsed time has not exceeded the output time (step S2U: NO), the processor 36 returns to step S2S, and continues the constant voltage control.

On the other hand, when it is determined that the elapsed time has exceeded the output time (step S2U: YES), the processor 36 stops supply of the output voltage to the heat transfer plate 13 and the counter plate 93 from the high-frequency-energy output unit 31 (step S2V). The processor 36 ends this control flow.

Heat Control

Next, a heat control (step S3) performed by the processor 36 will be explained. The heat control (step S3) is performed in parallel with the high frequency control (step S2) described above.

Figure 14:
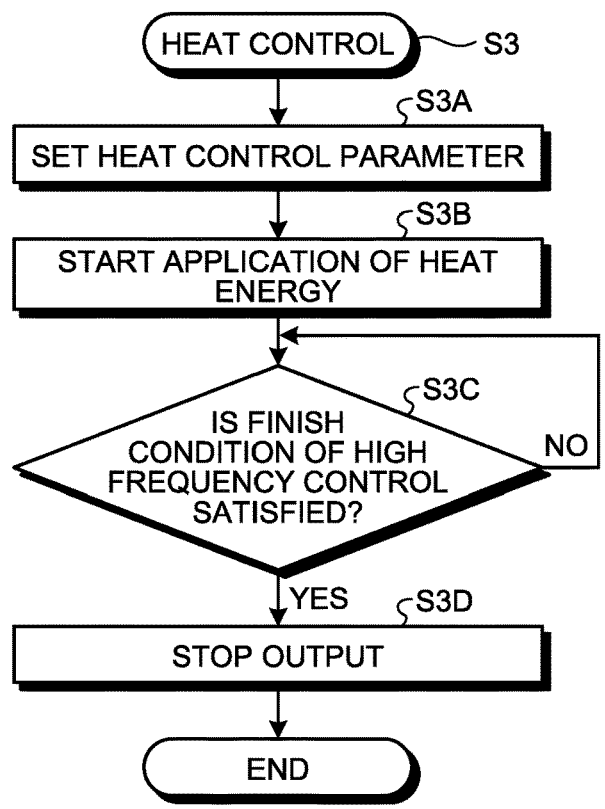
FIG. 14 is a flowchart of a heat control.

FIG. 14 is a flowchart of the heat control.

First, the processor 36 refers to a determination result of a residual heat level stored in the memory 37 and second reference information that has been stored in advance in the memory 37, and sets a heat control parameter (step S3A). Examples of the second reference information include information indicated in Table 2 below.

TABLE 2

| Heat control parameter | Determination result of residual heat level | | | |
|---|---|---|---|---|
| | No residual heat | Small | Medium | Large |
| Delay time [s] | 0 | 0 | 1 | Not output |

The second reference information is information in which a determination result of a residual heat level ("no residual heat", "small", "medium", "large") and a heat control parameter is associated with each other as indicated in Table 2.

The heat control parameter is a delay time [s] to delay a start time of application of a heat energy (step S3B) described later as indicated in Table 2. The heat control parameter corresponds to the control target value according to the present disclosure. That is, the processor 36 changes the control target value according to the present disclosure based on a determination result of a residual heat level. When the determination result of a residual heat level is "large", the application of the heat energy (step S3B) described later is not performed. Therefore, information indicating "not output" is set.

A value of the delay time is not limited to the value indicated in Table 2, but may take other values as long as it does not increase as the determination result of a residual heat level shifts as "large", "medium", "small", and to "no residual heat", that is, as the residual heat level decreases".

The processor 36 sets the delay time to 1 [s], for example, when the determination result of a residual heat level is "medium" at step S3A.

After step S3A, the processor 36 refers to the heat control parameter set at step S3A, and starts supply of the output voltage to the electrical resistance pattern constituting the heater 14 from the heat-energy output unit 33 (step S3B). That is, application of a heat energy to the target portion LT is started. Thus, heat is transferred to the target portion LT from the heat transfer plate 13, and the target portion LT is heated.

Specifically, the processor 36 performs following processing at step S3B.

The processor 36 calculates a resistance value of the electrical resistance pattern constituting the heater 14 based on the voltage value and the current value detected by the second sensor 34. Moreover, the processor 36 converts the resistance value of the electrical resistance pattern into a temperature (hereinafter, described as heater temperature) by using a relationship between a resistance value and a temperature of the electrical resistance pattern that have been calculated in advance based on experiments. The processor 36 supplies an output voltage necessary for bringing the heater temperature to a target temperature to the electrical resistance pattern from the heat-energy output unit 33 while grasping the heater temperature. That is, the processor 36 performs a feedback control.

When the determination result of a residual heat level is "no residual heat" or "small", and the heat control parameter (delay time) set at step S3A is 0 [s], the processor 36 starts application of a heat energy to the target portion LT at an original start time. Moreover, when the determination result of a residual heat level is "medium", and the heat control parameter (delay time) set at step S3A is 1 [s], the processor 36 starts application of a heat energy to the target portion LT at a point delayed by 1 [s] from the original start time. Furthermore, when the determination result of a residual heat level is "large", and the heat control parameter (delay time) set at step S3A is information indicating "not output", the processor 36 does not apply a heat energy to the target portion LT. That is, the processor 36 does not perform step S3B.

After step S3B, the processor 36 monitors whether a finish condition of the high frequency control (step S2) has been satisfied all the time (step S3C). In other words, the processor 36 monitors whether it has been determined as "YES" at step S2U described above all the time.

The processor 36 continues application of the heat energy to the target portion LT until it is determined that the finish condition of the high frequency control (step S2) is satisfied (step S3C: YES). Moreover, when it is determined that the finish condition of the high frequency control (step S2) is satisfied (step S3C: YES), the processor 36 stops supply of the output voltage to the electrical resistance pattern constituting the heater 14 from the heat-energy output unit 33 (step S3D). The processor 36 then ends this control flow.

By the high frequency control (step S2) and the heat control (step S3) described above, the target portion LT is heated at a first temperature of, for example, approximately 100° C. to 200° C. necessary for sealing. Thus, the target portion LT is sealed.

According to the present embodiment described above, following effects are produced.

In the treatment system 1 according to the present embodiment, the processor 36 calculates an impedance of the target portion LT to be an index of temperature of the heat transfer plate 13 and the counter plate 93 before application of a high frequency energy and a heat energy (steps S2E, S3B) to the target portion LT (step S1B). Moreover, the processor 36 determines a residual heat level of the heat transfer plate 13 and the counter plate 93 based on the impedance of the target portion LT (steps S1E, S1G, S1I, S1J). The processor 36 then performs notification of information indicating a warning from the notifying unit 35 (step S1M), and adjustment of a power to be supplied to the grasping portion 7 (steps S2D, S2R, S3A) based on the determination result of a residual heat level.

Accordingly, it is possible to avoid the target portion LT from being excessively heated when the target portion LT is sealed in a state in which the residual heat level of the heat transfer plate 13 and the counter plate 93 is high. That is, heat invasion to a living tissue, erroneous incision of the target portion LT, a negative effect on the sealing performance for the target portion LT, and the like can be avoided.

Particularly, an impedance of the target portion LT is used as an index value to be an index for temperature of the heat transfer plate 13 and the counter plate 93.

Therefore, for example, compared with a configuration in which a residual heat level is determined based on heater temperature, a degree of influence (thermal denaturation level) on the target portion LT by the residual heat of the heat transfer plate 13 and the counter plate 93 can actually be seen by the impedance of the target portion LT. That is, it is possible to appropriately determine whether the target portion LT is to be excessively heated.

In the treatment system 1 according to the present embodiment, the processor 36 performs determination of a residual heat level (steps S1E, S1G, S1I, S1J) after the setting operation of the sealing control (step S1C: YES) with respect to the second switch 522. That is, the processor 36 performs determination of a residual heat level (steps S1E, S1G, S1I, S1J) before application of the high frequency energy and the heat energy to the target portion LT (steps S2E, S3B).

Therefore, by performing the processing described above (steps S1M, S2D, S2R, S3A) in the sealing control mode susceptible to residual heat of the heat transfer plate 13 and the counter plate 93, it is possible to appropriately avoid the target portion LT from being excessively heated.

In the treatment system 1 according to the present embodiment, the processor 36 reduces a power to be supplied to the heat transfer plate 13 and the counter plate 93 to be less (steps S2D, S2R) as the residual heat level increases. Moreover, the processor 36 adjusts a power to be supplied to the heat transfer plate 13 and the counter plate 93 based on a determination result of a residual heat level in the sealing control mode (steps S2D, S2R).

Therefore, it is possible to appropriately avoid the target portion LT from being excessively heated.

In the treatment system 1 according to the present embodiment, the processor 36 causes the notifying unit 35 to notify of information indicating a warning when the residual heat level exceeds a specific level. Furthermore, the processor 36 inhibits supply of power to the holding portion 7.

Therefore, it is possible to certainly prevent the target portion LT from being excessively heated while making the operator aware that the high frequency energy and the heat energy to the target portion LT cannot be applied because the target portion LT is to be excessively heated.

In the treatment system 1 according to the present embodiment, the processor 36 determines a type and a size ("adipose tissue", "blood vessel of size S", "blood vessel of size L") of the target portion LT by flowing a detection current to the target portion LT (steps S2K, S2N, S2O). The processor 36 then adjusts a power to be supplied to the heat transfer plate 13 and the counter plate 93 based on the determination result of a residual heat level and the tissue determination result (step S2R).

Therefore, it is possible to appropriately avoid a blood vessel of size S particularly sensitive to temperature from being excessively heated.

Other Embodiments

The embodiment to implement the present disclosure has been explained hereinabove, but the present disclosure is not limited to be implemented by the embodiment described above.

Figure 15:
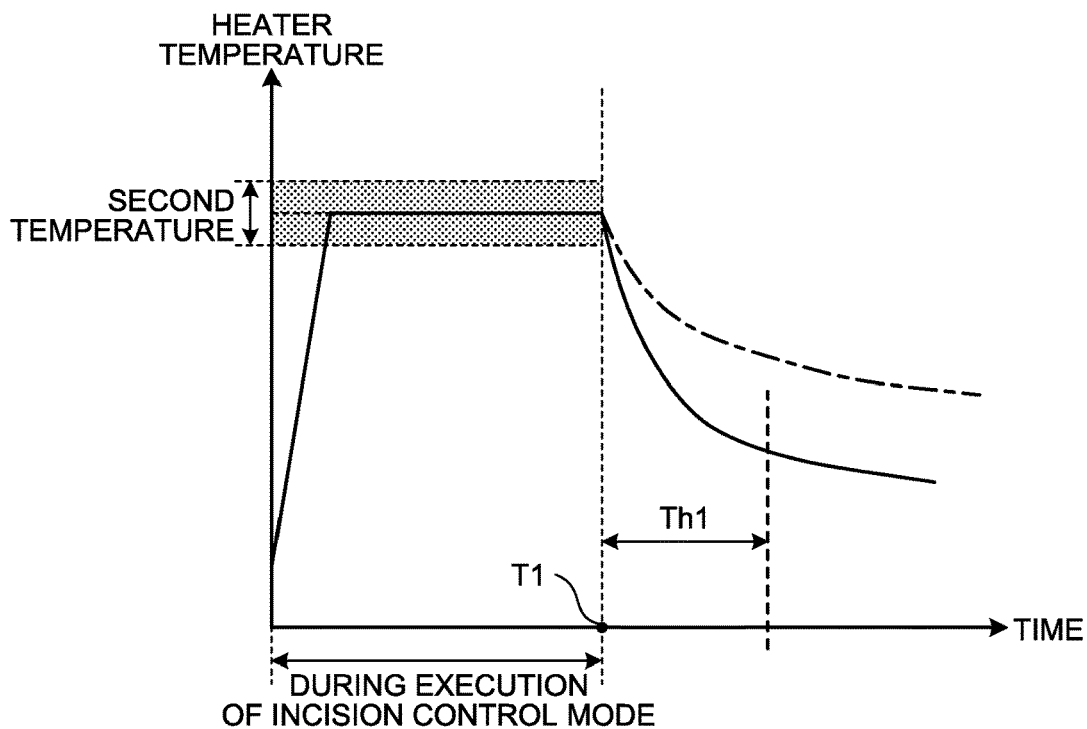
FIG. 15 illustrates an exemplary embodiment.
Figure 16:
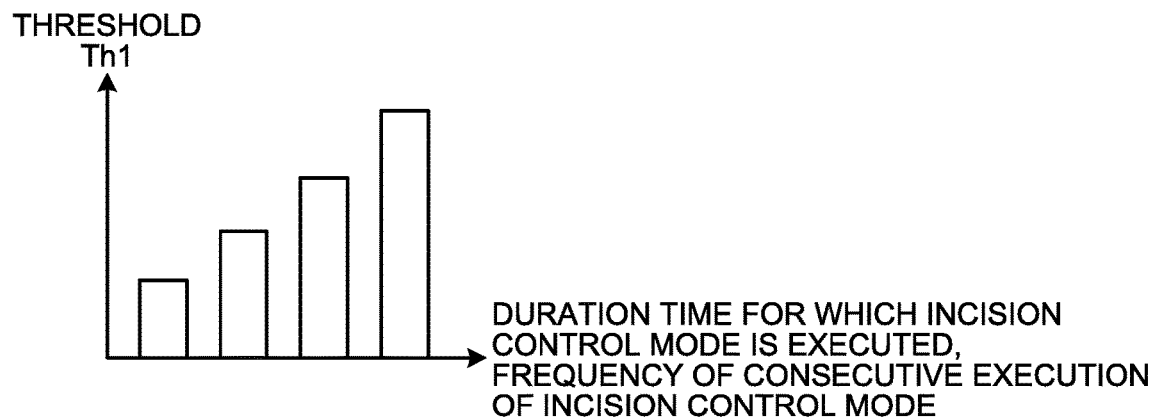
FIG. 16 illustrates an exemplary embodiment.

FIG. 15 and FIG. 16 illustrate a first modification of the present disclosure. Specifically, FIG. 15 shows a behavior of heater temperature during and after the incision control mode. FIG. 16 shows a threshold used for determination of a residual heat level.

In the embodiment described above, the residual heat determination method to determine a residual heat of the heat transfer plate 13 and the counter plate 93 is not limited to the control flow illustrated in FIG. 4 and FIG. 5.

The heater temperature gradually increases when execution of the incision control mode is started as shown in FIG. 15. The heater temperature is controlled to the second temperature of approximately 300° C. necessary to incise the target portion LT. Moreover, when execution of the incision control mode is finished, the heater temperature decreases as time elapses from a time T1 (FIG. 15) at which the execution is finished.

Accordingly, the processor 36 measures elapsed time from the time T1. When the measured elapsed time exceeds a threshold Th1 (FIG. 15), the processor 36 determines the residual heat level of the heat transfer plate 13 and the counter plate 93 as "no residual heat". On the other hand, when the measured elapsed time is equal to or shorter than the threshold Th1, the processor 36 determines the residual heat level as "residual heat remains". That is, the processor 36 determines a residual heat level after the incision control mode is executed.

In the first modification, the elapsed time is measured from the time T1 at which the execution of the incision mode is finished, but it is not limited thereto, and elapsed time after the heater temperature reaches the second temperature may be measured. The residual heat level may be determined by comparing the elapsed time and the threshold Th1.

Moreover, the residual heat level may be determined based on a comparison result between the amount of change Zch and the residual-heat determination thresholds Zj1, Zj2 explained in the above embodiment, and a comparison result between the elapsed time and the threshold Th1 in the first modification. That is, the residual-heat determination thresholds Zj1, Zj2 correspond to a second threshold according to the present disclosure. Moreover, the threshold Th1 corresponds to a first threshold according to the present disclosure.

Furthermore, in the first modification, the residual heat level has two levels including "no residual heat" and "residual heat remains", but it is not limited thereto. By providing multiple values of the thresholds Th1, the residual heat level may have three or more levels. Moreover, the residual heat level has four levels including "no residual heat", "small", "medium", and "large" in the embodiment described above also, but it is not limited thereto, and it may have two, three, or five or more levels.

The longer the duration time for which the incision control mode is executed is, and the more the frequency of consecutive execution of the incision control mode is, the less the amount of reduction of the heat temperature from the time T1 at which execution of the incision control mode is finished becomes, as indicated by an alternate long and short dash line in FIG. 15.

Therefore, as shown in FIG. 16, a larger value of the threshold Th1 may be used as the threshold Th1, as the duration in which the incision control mode is executed increases, or as the frequency of consecutive execution of the incision control mode increases.

Figure 17:
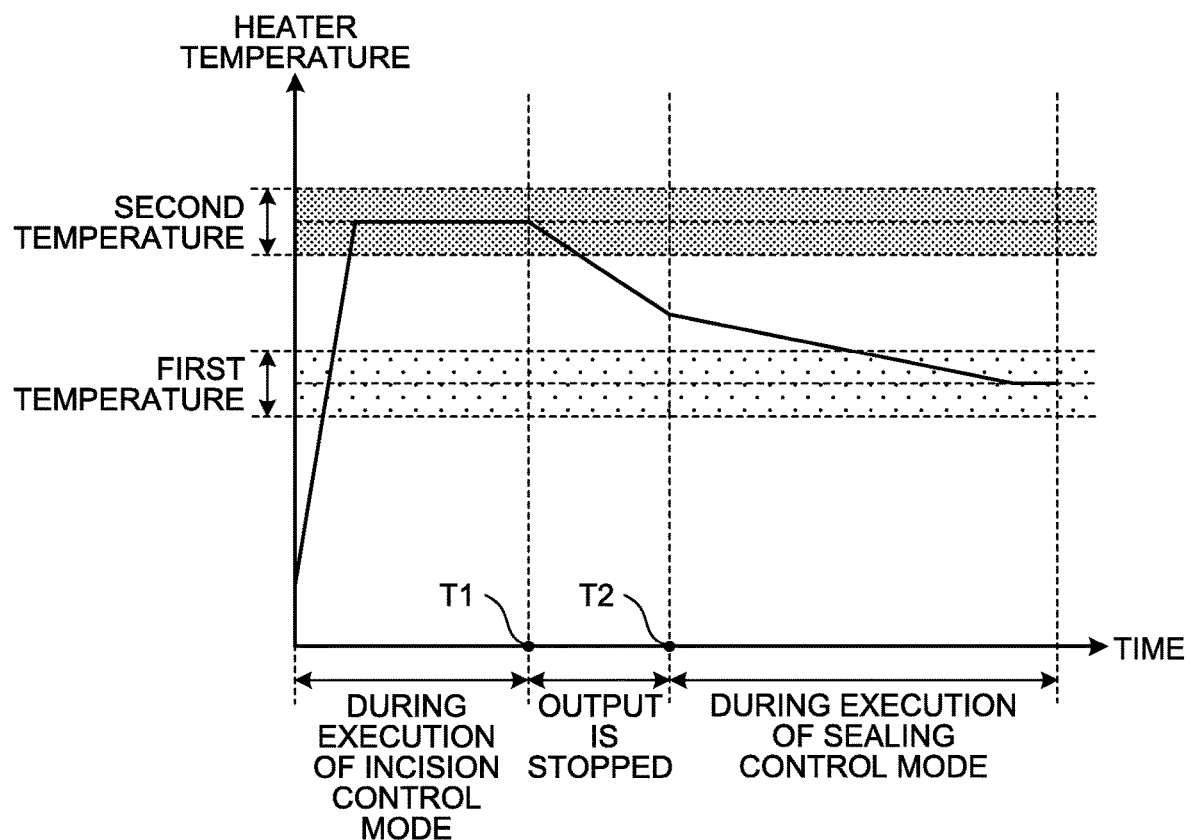
FIG. 17 illustrates an exemplary embodiment.

FIG. 17 is a second modification of the present embodiment. Specifically, FIG. 17 shows a behavior of heater temperature when the sealing control mode is executed after the incision control mode is executed.

In the embodiment described above, the residual heat determining method to determine a residual heat level of the heat transfer plate 13 and the counter plate 93 is not limited to the flow shown in FIG. 4 and FIG. 5, but the residual heat level may be determined based on heater temperature. That is, the heater temperature corresponds to the index value according to the present disclosure.

For example, as shown in FIG. 17, a case in which the heater temperature at a time T2 at which the sealing control mode is started after the incision control mode is executed exceeds the first temperature of approximately 100° C. to 200° C. necessary for sealing the target portion LT is assumed. In this case, the processor 36 determines the residual heat level of the heat transfer plate 13 and the counter plate 93 as "residual heat remains". On the other hand, when the heater temperature at the time T2 is equal to or lower than the first temperature, the processor 36 determines the residual heat level as "no residual heat".

In the second modification, the residual heat level has two levels including "no residual heat" and "residual heat remains", but by providing multiple reference temperatures to be compared with the heater temperature, the residual heat level may have three or more levels.

Figure 18:
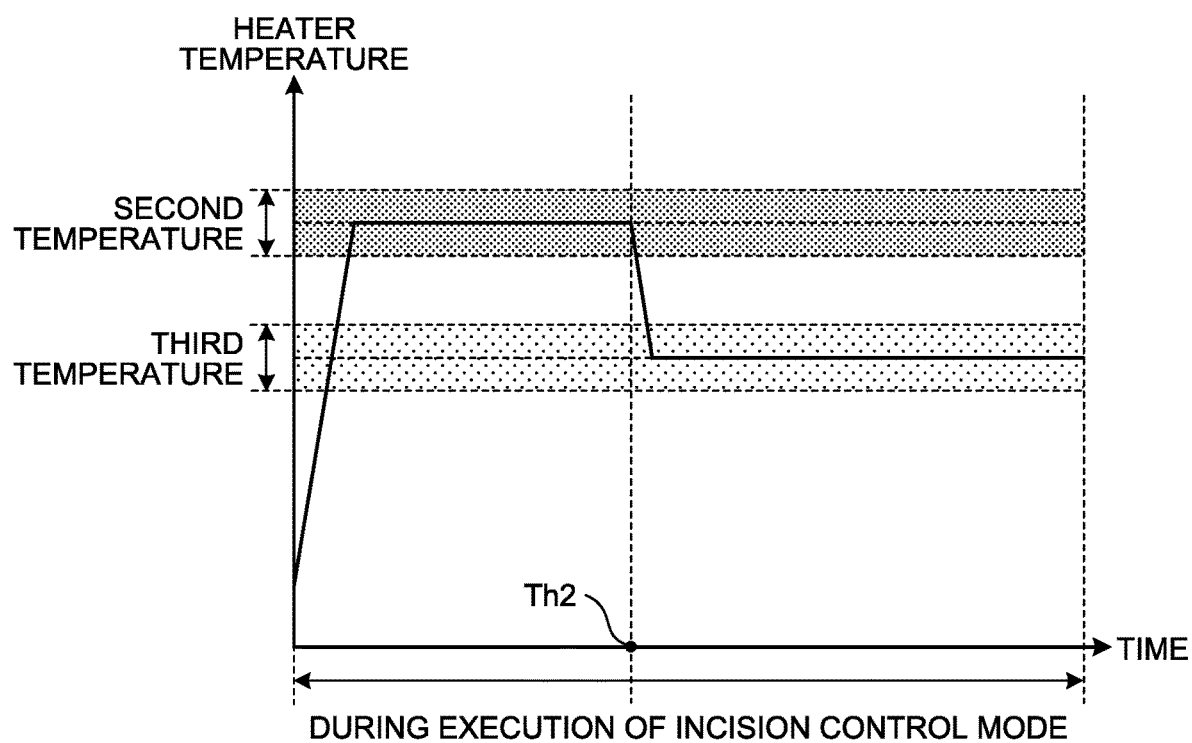
FIG. 18 illustrates an exemplary embodiment.

FIG. 18 illustrates a third modification of the present embodiment. Specifically, FIG. 18 shows a behavior of heat temperature during execution of the incision control mode.

In the embodiment described above, when the elapsed time since execution of the incision control mode is started exceeds a threshold Th2 as shown in FIG. 18, the target temperature of the heater temperature in the incision control mode may be changed from the second temperature of approximately 300° C. to a third temperature of approximately 250° C. lower than the second temperature.

Thus, the residual heat of the heat transfer plate 13 and the counter plate 93 itself after execution of the incision control mode is finished can be reduced.

In the embodiment described above, the second reference information is not limited to information indicated in Table 2, but may use information indicated in Table 3 below.

TABLE 3

| Heat control parameter | Determination result of residual heat level | | | |
|---|---|---|---|---|
| | No residual heat | Small | Medium | Large |
| Duty ratio [%] | 100 | 100 | 50 | Not output |

The second reference information is information in which a determination result of a residual heat level ("no residual heat", "small", "medium", and "large") and a heat control parameter are associated with each other as indicated in Table 3.

The heat control parameter is a duty ratio [%] when an output voltage is supplied to the electrical resistance pattern constituting the heater 14 from the heat-energy output unit 33 at step S3B as indicated in Table 3. The heat control parameter corresponds to a control target value according to the present disclosure. That is, the processor 36 changes the control target value according to the present disclosure based on a determination result of a residual heat level. Because application of the heat energy (step S3B) is not performed when the residual heat level is "large", information indicating "not output" is set.

A value of the duty ratio is not limited to the values indicated in Table 3, but other values may be used as long as the value does not decrease as the determination result of the residual heat level changes from "large", "medium", "small", and then "no residual heat", that is, as the residual heat level decreases.

The processor 36 then performs following processing at step S3B.

When the determination result of a residual heat level is "no residual heat" or "small", and the heat control parameter (duty ratio) set at step S3A is 100 [%], the processor 36 keeps supplying the output voltage necessary for bringing the heater temperature to a target temperature from the heat-energy output unit 33 to the electrical resistance pattern constituting the heater 14. Moreover, when the determination result of a residual heat level is "medium" and the heat control parameter (duty ratio) set at step S3A is 50 [%], the processor 36 supplies the output voltage necessary for bringing the heater temperature to a target temperature from the heat-energy output unit 33 intermittently according to the duty ratio to the electrical resistance pattern. Furthermore, when the determination result of a residual heat level is "large" and the heat control parameter (duty ratio) set at step S3A is information indicating "not output", the processor 36 does not output a heat energy to the target portion LT. That is, the processor 36 does not perform step S3B.

The second reference information is not limited to the information indicated in Table 2 and Table 3, but information indicated in Table 4 below may be used.

TABLE 4

| Heat control parameter | Determination result of residual heat level | | | |
|---|---|---|---|---|
| | No residual heat | Small | Medium | Large |
| Target temperature [° C.] | 120 | 120 | 80 | Not output |

The second reference information is information in which a determination result of a residual heat level ("no residual heat", "small", "medium", "large") and a heat control parameter is associated with each other as indicated in Table 4.

The heat control parameter is a target temperature [C °] of the heater temperature used at step S3B as indicated in Table 4. The heat control parameter corresponds to a control target value according to the present disclosure. That is, the processor 36 changes the control target value according to the present disclosure based on a determination result of a residual heat level. Because application of a heat energy (step S3B) is not performed when a determination result of a residual heat level is "large", the information indicating "not output" is set.

A values of the target temperature are not limited to the values indicated in Table 4, but other values can be used as long as the value does not decrease as the determination result of a residual heat level changes from "large", "medium", "small", and then "no residual heat", that is, as the residual heat level decreases.

The processor 36 then performs following processing at step S3B.

When the determination result of a residual heat level is "no residual heat" or "small", and the heat control parameter (target temperature) set at step S3A is 120 [° C.], the processor 36 supplies the output voltage necessary for bringing the heater temperature to 120 [° C.] from the heat-energy output unit 33 to the electrical resistance pattern constituting the heater 14. Moreover, when the determination result of a residual heat level is "medium" and the heat control parameter (target temperature) set at step S3A is 80 [° C.], the processor 36 supplies the output voltage necessary for bringing the heater temperature to 80 [° C.] from the heat-energy output unit 33 according to the duty ratio to the electrical resistance pattern. Furthermore, when the determination result of a residual heat level is "large" and the heat control parameter (target temperature) set at step S3A is information indicating "not output", the processor 36 does not output a heat energy to the target portion LT. That is, the processor 36 does not perform step S3B.

As described above, the processor 36 adjusts a power to be supplied to the electrical resistance pattern based on a determination result of a residual heat level in the sealing control mode.

In the embodiment described above, the processor according to the present disclosure is constituted of a single unit of the processor 36, but it is not limited thereto, and two or more processors may be used.

In the embodiment described above, the notifying unit 35 may be configured to notify of information indicating a residual heat level after determination of the residual heat level is performed (step S1E, S1G, S1I, S1J).

In the embodiment described above, a configuration in which at least one of the heat energy and the high frequency energy is selected as a treatment energy to be applied to the target portion LT based on a determination result of a residual heat level may be adopted. For example, the processor 36 selects both the heat energy and the high frequency energy as the treatment energy to be applied to the target portion LT when the residual heat level is a first level. On the other hand, the processor 36 selects one out of the heat energy and the high frequency energy as the treatment energy to be applied to the target portion LT when the residual heat level is a second level higher than the first level.

In the embodiment described above, the heat energy and the high frequency energy are used as the treatment energy to be applied to the target portion LT, but it is not limited thereto, and an ultrasonic energy may be used. Note that "applying an ultrasonic energy to the target portion LT" means that applying ultrasonic vibrations to the target portion. When the ultrasonic energy is used, examples of control target value changed based on a determination result of a residual heat level include following control target values.

For example, as the control target value, delay time by which a start time of application of the ultrasonic energy is delayed may be used similarly to the heat control parameter used in the heat control (step S3) explained in the embodiment above. Moreover, for example, as the control target value, an amplitude by ultrasonic vibrations may be used.

The control device, the treatment system, the residual-heat determining method, and the computer readable recording medium according to the present disclosure enables to avoid a living tissue from being excessively heated.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device for being used with a treatment tool including an end effector configured to apply a treatment energy to a living tissue for treatment of the living tissue, the control device comprising: a processor configured to: execute a sealing control mode in which electrical power to seal the living tissue by heating the living tissue at a first temperature is supplied to the end effector, and an incision control mode in which electrical power to incise the living tissue by heating the living tissue at a second temperature that is higher than the first temperature is supplied to the end effector; calculate elapsed time as a first index value for a temperature of the end effector, the elapsed time beginning at a time when the end effector reaches the second temperature; calculate an impedance level at a treatment target of the living tissue; determine a change in the impedance level between the calculated impedance level and an initial impedance; compare the change in the impedance level to a predetermined residual heat-determination threshold impedance level to obtain a first comparison result; compare the first index value and a first threshold value to obtain a second comparison result; determine a residual heat level of the end effector based on the first comparison result and the second comparison result such that a low residual heat is determined when the change in the impedance level is less than the predetermined residual heat-determination threshold impedance level and a high residual heat is determined when the change in the impedance level is equal to or higher than the predetermined residual heat-determination threshold impedance level; and perform, based on the determined residual heat level, at least one of the following: issuance of a warning from a notifying unit; or adjustment of electrical power supplied to the end effector.

2. The control device according to claim 1, further comprising:
an interface configured to receive a start operation for application of the treatment energy, wherein:
the processor is configured to determine the residual heat level after the interface receives the start operation.

3. The control device according to claim 1 wherein the processor is configured to determine the residual heat level after the incision control mode is executed.

4. The control device according to claim 1, wherein the processor is configured to determine the residual heat level in the sealing control mode.

5. The control device according to claim 4, wherein the processor is configured to adjust the electrical power supplied to the end effector based on the residual heat level in the sealing control mode.

6. The control device according to claim 5, wherein the processor is configured to change a control target value in the sealing control mode based on the residual heat level.

7. The control device according to claim 5, wherein the processor is configured to:
determine at least one of a type or a size of the living tissue; and
adjust the electrical power supplied to the end effector based on the residual heat level and the at least one type or size of the living tissue.

8. The control device according to claim 1, wherein the elapsed time is elapsed time since the incision control mode is completed.

9. The control device according to claim 1, wherein
the processor is configured to store a plurality of threshold values corresponding to at least one of duration time for which the incision control mode is executed or a frequency of consecutive execution of the incision control mode, and
the processor is configured to compare one of the threshold values corresponding to at least either one of the duration time and the frequency with the elapsed time.

10. The control device according to claim 1, wherein the processor is configured to cause the notifying unit to notify of information indicating the residual heat level.

11. The control device according to claim 1, wherein the processor is configured to reduce the electrical power supplied to the end effector as the residual heat level increases.

12. The control device according to claim 1, wherein the processor is configured to inhibit supply of the electrical power to the end effector when the residual heat level exceeds a predetermined level.

13. The control device according to claim 1, wherein the processor is configured to cause the notifying unit to notify of information indicating the warning when the residual heat level exceeds a predetermined level.

14. A treatment system comprising:
the control device according to claim 1; and
the end effector configured to apply treatment energy to living tissue for treatment of the living tissue, the end effector including a pair of high frequency electrodes, wherein the control device further includes:
a high-frequency-energy output unit configured to apply high frequency energy that is the treatment energy to the living tissue from the end effector by supplying the power between the pair of high frequency electrodes, and
the processor is configured to control an operation of the high-frequency-energy output unit, and determine at least one of a type and a size of the living tissue by flowing a detection current to the living tissue from the end effector.

15. The control device according to claim 1, wherein the processor is configured to determine when there is no residual heat.

16. The control device according to claim 1, wherein the processor is configured to, based on the determined residual heat level, issue the warning from the notifying unit and adjust the electrical power supplied to the end effector.

17. The control device according to claim 1, wherein the processor is configured to determine that there is no residual heat when the change from the initial impedance is smaller than a second predetermined residual-heat determination threshold impedance level.

18. A method of determining a residual heat level, the method comprising: executing a sealing control mode in which electrical power configured to seal a living tissue by heating the living tissue at a first temperature is supplied to an end effector, and an incision control mode in which electrical power to incise the living tissue by heating the living tissue at a second temperature that is higher than the first temperature is supplied to the end effector; calculating elapsed time as an index value for a temperature of the end effector, the elapsed time beginning at a time when the temperature of the end effector reaches the second temperature; calculating an impedance level at a treatment target of the living tissue; determining a change in the impedance level between the calculated impedance level and an initial impedance; comparing the change in the impedance level to a predetermined residual heat-determination threshold impedance level to obtain a first comparison result; comparing the index value and a threshold value to obtain a second comparison result; determining the residual heat level of the end effector based on the first comparison result and the second comparison result such that low residual heat is determined when the change in the impedance level is less than the predetermined residual heat-determination threshold impedance level and high residual heat is determined when the change in the impedance level is equal to or higher than the predetermined residual heat-determination threshold impedance level; and performing, based on the residual heat level, at least one of: issuance of a warning from a notifying unit; or adjustment of electrical power supplied to the end effector.

19. A non-transitory computer-readable recording medium on which an executable program is recorded, the program causing a processor of a computer to: execute a sealing control mode in which electrical power to seal a living tissue by heating the living tissue at a first temperature is supplied to an end effector, and an incision control mode in which electrical power to incise the living tissue by heating the living tissue at a second temperature that is higher than the first temperature is supplied to the end effector; calculate elapsed time as an index value for a temperature of the end effector, the elapsed time beginning at a time when the temperature of the end effector reaches the second temperature; calculate an impedance level at a treatment target of the living tissue; determine a change in the impedance level between the calculated impedance level and an initial impedance; compare the change in the impedance level to a predetermined residual heat-determination threshold impedance level to determine a first comparison result; compare the index value and a threshold value to obtain a second comparison result; determine a residual heat level of the end effector based on the first comparison result and the second comparison result such that a low residual heat is determined when the change in the impedance level is less than the predetermined residual heat-determination threshold impedance level and a high residual heat is determined when the change in the impedance level is equal to or higher than the predetermined residual heat-determination threshold impedance level; and perform, based on the residual heat level, at least one of: notification of information indicating a warning from a notifying unit; or adjustment of electrical power supplied to the end effector.

* * * * *